US012428577B2

(12) United States Patent
Schmitt

(10) Patent No.: US 12,428,577 B2
(45) Date of Patent: Sep. 30, 2025

(54) METHODS OF MONITORING IN VITRO TRANSCRIPTION OF mRNA AND/OR POST-IN VITRO TRANSCRIPTION PROCESSES

(71) Applicant: ModernaTX, Inc., Cambridge, MA (US)

(72) Inventor: Elliott Schmitt, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 18/560,444

(22) PCT Filed: May 12, 2022

(86) PCT No.: PCT/US2022/028969
§ 371 (c)(1),
(2) Date: Nov. 13, 2023

(87) PCT Pub. No.: WO2022/241103
PCT Pub. Date: Nov. 17, 2022

(65) Prior Publication Data
US 2024/0263226 A1  Aug. 8, 2024

Related U.S. Application Data

(60) Provisional application No. 63/188,583, filed on May 14, 2021.

(51) Int. Cl.
| | |
|---|---|
| *C12Q 1/6851* | (2018.01) |
| *C08K 3/34* | (2006.01) |
| *C09D 5/14* | (2006.01) |
| *C09D 7/61* | (2018.01) |
| *C09D 133/08* | (2006.01) |
| *C09D 175/04* | (2006.01) |
| *C12Q 1/6865* | (2018.01) |

(52) U.S. Cl.
CPC .............. *C09D 133/08* (2013.01); *C08K 3/34* (2013.01); *C09D 5/14* (2013.01); *C09D 7/61* (2018.01); *C09D 175/04* (2013.01); *C12Q 1/6851* (2013.01); *C12Q 1/6865* (2013.01)

(58) Field of Classification Search
CPC .................. C12Q 1/6865; C12Q 2565/632
See application file for complete search history.

(56) References Cited

U.S. PATENT DOCUMENTS

| | | |
|---|---|---|
| 7,335,471 B2 | 2/2008 | Guillerez et al. |
| 8,710,200 B2 | 4/2014 | Schrum et al. |
| 8,754,062 B2 | 6/2014 | De Fougerolles et al. |
| 8,822,663 B2 | 9/2014 | Schrum et al. |
| 8,980,864 B2 | 3/2015 | Hoge et al. |
| 8,999,380 B2 | 4/2015 | Bancel et al. |
| 9,012,219 B2 | 4/2015 | Kariko et al. |
| 9,045,740 B2 | 6/2015 | Martin et al. |
| 9,163,246 B2 | 10/2015 | Barnes |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,464,124 B2 | 10/2016 | Bancel et al. |
| 9,512,456 B2 | 12/2016 | Wang et al. |
| 9,533,047 B2 | 1/2017 | de Fougerolles et al. |
| 9,572,896 B2 | 2/2017 | Bancel et al. |
| 9,597,380 B2 | 3/2017 | Chakraborty et al. |
| 9,675,668 B2 | 6/2017 | Bancel et al. |
| 9,868,691 B2 | 1/2018 | Benenato et al. |
| 9,872,900 B2 | 1/2018 | Ciaramella et al. |
| 10,023,626 B2 | 7/2018 | Bolen et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,323,076 B2 | 6/2019 | Ellsworth et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,881,730 B2 | 1/2021 | Huang et al. |

(Continued)

FOREIGN PATENT DOCUMENTS

| | | |
|---|---|---|
| WO | WO 95/08626 A1 | 3/1995 |
| WO | WO 2023/201204 A1 | 10/2003 |

(Continued)

OTHER PUBLICATIONS

International Search Report and Written Opinion for International Application No. PCT/US2022/028969, mailed Sep. 12, 2022.
Bonhommeau et al., Tip-Enhanced Raman Spectroscopy: A Tool for Nanoscale Chemical and Structural Characterization of Biomolecules. ChemPhysChem. Jan. 5, 2018;19(1):8-18.
Chen et al., Characterizing RNA structure and synthesis by Raman microscopy, Dissertation Abstracts International. vol. Feb. 6, 2010 (Feb. 6, 2010), pp. 1-182.
Hobro et al., Raman and Raman optical activity (ROA) analysis of RNA structural motifs in Domain I of the EMCV IRES. Nucleic Acids Res. Feb. 2007; 35(4): 1169-1177.
Liu et al., Real-time monitoring in vitro transcription using molecular beacons. Anal Biochem. Jan. 1, 2002;300(1):40-5. doi: 10.1006/abio.2001.5446.

(Continued)

*Primary Examiner* — Young J Kim
(74) *Attorney, Agent, or Firm* — Wolf, Greenfield & Sacks, P.C.

(57) ABSTRACT

Methods of monitoring in vitro transcription of mRNA and/or post-in vitro transcription processes are provided. For example, methods of monitoring in vitro transcription of mRNA and/or post-in vitro transcription processes by acquiring one or more Raman spectra are provided.

30 Claims, 10 Drawing Sheets

(56) References Cited

U.S. PATENT DOCUMENTS

| | | |
|---|---|---|
| 10,925,958 B2 | 2/2021 | Ciaramella |
| 11,027,025 B2 | 6/2021 | Hoge et al. |
| 11,045,540 B2 | 6/2021 | Ciaramella |
| 11,103,578 B2 | 8/2021 | Ciaramella et al. |
| 11,351,242 B1 | 6/2022 | Lori et al. |
| 11,384,352 B2 | 7/2022 | Miracco |
| 11,406,703 B2 | 8/2022 | Kramarczyk et al. |
| 11,464,848 B2 | 10/2022 | Ciaramella et al. |
| 11,485,960 B2 | 11/2022 | Dousis et al. |
| 11,497,807 B2 | 11/2022 | Ciaramella et al. |
| 11,564,893 B2 | 1/2023 | Smith |
| 11,576,961 B2 | 2/2023 | Ciaramella et al. |
| 11,643,441 B1 | 5/2023 | Ciaramella et al. |
| 11,696,946 B2 | 7/2023 | Ciaramella |
| 11,752,206 B2 | 9/2023 | Ciaramella et al. |
| 11,786,607 B2 | 10/2023 | Hoge et al. |
| 11,851,694 B1 | 12/2023 | Mauger et al. |
| 11,866,696 B2 | 1/2024 | Issa et al. |
| 11,872,278 B2 | 1/2024 | Ciaramella et al. |
| 11,905,525 B2 | 2/2024 | Brito et al. |
| 11,911,453 B2 | 2/2024 | Ciaramella et al. |
| 11,912,982 B2 | 2/2024 | Issa et al. |
| 12,070,495 B2 | 8/2024 | Lusso et al. |
| 12,151,029 B2 | 11/2024 | Hennessy et al. |
| 2007/0037245 A1 | 2/2007 | Endo et al. |
| 2013/0059344 A1 | 3/2013 | Striedner et al. |
| 2013/0102034 A1 | 4/2013 | Schrum et al. |
| 2013/0236974 A1 | 9/2013 | De Fougerolles |
| 2013/0245103 A1 | 9/2013 | de Fougerolles et al. |
| 2013/0259923 A1 | 10/2013 | Bancel et al. |
| 2013/0266640 A1 | 10/2013 | De Fougerolles et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2015/0376581 A1 | 12/2015 | Brakmann et al. |
| 2016/0024140 A1 | 1/2016 | Issa et al. |
| 2016/0024141 A1 | 1/2016 | Issa et al. |
| 2016/0032261 A1 | 2/2016 | Sobek et al. |
| 2016/0032273 A1 | 2/2016 | Shahrokh et al. |
| 2016/0032316 A1 | 2/2016 | Weissman et al. |
| 2016/0038612 A1 | 2/2016 | Hoge et al. |
| 2016/0194368 A1 | 7/2016 | Hoge et al. |
| 2016/0194625 A1 | 7/2016 | Hoge et al. |
| 2016/0243221 A1 | 8/2016 | Hoge et al. |
| 2016/0317647 A1 | 11/2016 | Ciaramella et al. |
| 2017/0043037 A1 | 2/2017 | Kariko et al. |
| 2017/0130255 A1 | 5/2017 | Wang et al. |
| 2017/0202979 A1 | 7/2017 | Chakraborty et al. |
| 2017/0204152 A1 | 7/2017 | Nelson et al. |
| 2018/0000953 A1 | 1/2018 | Almarsson et al. |
| 2018/0002393 A1 | 1/2018 | Bancel et al. |
| 2018/0028664 A1 | 2/2018 | Besin et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |
| 2018/0289792 A1 | 10/2018 | Ciaramella et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0125839 A1 | 5/2019 | Frederick et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0314493 A1 | 10/2019 | Ciaramella et al. |
| 2019/0336452 A1 | 11/2019 | Brader |
| 2019/0336595 A1 | 11/2019 | Ciaramella |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129445 A1 | 4/2020 | Patel et al. |
| 2020/0129608 A1 | 4/2020 | Ciaramella et al. |
| 2020/0129615 A1 | 4/2020 | Ciaramella et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0306191 A1 | 10/2020 | Schariter et al. |
| 2020/0338004 A1 | 10/2020 | Hansson et al. |
| 2020/0368162 A1 | 11/2020 | Martini |
| 2021/0046173 A1 | 2/2021 | Ciaramella et al. |
| 2021/0087135 A1 | 3/2021 | Benenato et al. |
| 2021/0163919 A1 | 6/2021 | Issa et al. |
| 2021/0187097 A1 | 6/2021 | Ciaramella et al. |
| 2021/0206818 A1 | 7/2021 | Huang et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0309976 A1 | 10/2021 | Dousis et al. |
| 2021/0378980 A1 | 12/2021 | Horhota et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0062175 A1 | 3/2022 | Smith et al. |
| 2022/0062408 A1 | 3/2022 | Kramarczyk et al. |
| 2022/0125899 A1 | 4/2022 | Ashburn et al. |
| 2022/0145381 A1 | 5/2022 | Elich et al. |
| 2022/0236253 A1 | 7/2022 | Hopson |
| 2022/0241399 A1 | 8/2022 | Lusso et al. |
| 2022/0347292 A1 | 11/2022 | Panther et al. |
| 2022/0348900 A1 | 11/2022 | Shamashkin et al. |
| 2022/0349006 A1 | 11/2022 | Amato et al. |
| 2023/0000970 A1 | 1/2023 | Nachbagauer et al. |
| 2023/0142529 A1 | 5/2023 | White et al. |
| 2023/0181481 A1 | 6/2023 | White et al. |
| 2023/0190761 A1 | 6/2023 | Brader et al. |
| 2023/0212645 A1 | 7/2023 | Marquardt et al. |
| 2023/0287437 A1 | 9/2023 | Smith et al. |
| 2023/0338506 A1 | 10/2023 | Shaw et al. |
| 2023/0346914 A1 | 11/2023 | Stewart-Jones et al. |
| 2023/0355743 A1 | 11/2023 | Stewart-Jones et al. |
| 2024/0100145 A1 | 3/2024 | Bollman et al. |
| 2024/0100151 A1 | 3/2024 | Carfi et al. |
| 2024/0139309 A1 | 5/2024 | Carfi et al. |
| 2024/0173400 A1 | 5/2024 | Ciaramella et al. |
| 2024/0181030 A1 | 6/2024 | Himansu et al. |
| 2024/0207392 A1 | 6/2024 | Chandramouli et al. |
| 2024/0209068 A1 | 6/2024 | Deal et al. |
| 2024/0226028 A1 | 7/2024 | Goldman et al. |

(56) References Cited

U.S. PATENT DOCUMENTS

| | | |
|---|---|---|
| 2024/0226277 A1 | 7/2024 | Nachbagauer et al. |
| 2024/0229109 A1 | 7/2024 | Rabideau et al. |
| 2024/0238211 A1 | 7/2024 | Brader et al. |
| 2024/0263226 A1 | 8/2024 | Schmitt |
| 2024/0285754 A1 | 8/2024 | Stewart-Jones |
| 2024/0293534 A1 | 9/2024 | Stewart-Jones |
| 2024/0299531 A1 | 9/2024 | Stewart-Jones |
| 2024/0358819 A1 | 10/2024 | Stewart-Jones |
| 2024/0368580 A1 | 11/2024 | Geng et al. |
| 2024/0382581 A1 | 11/2024 | Stewart-Jones et al. |
| 2024/0383940 A1 | 11/2024 | Endo et al. |
| 2024/0425902 A1 | 12/2024 | Smith |
| 2025/0011798 A1 | 1/2025 | Smith et al. |

FOREIGN PATENT DOCUMENTS

| | | | |
|---|---|---|---|
| WO | | 2013/050609 A1 | 4/2013 |
| WO | | 2013/090648 A1 | 6/2013 |
| WO | | 2014/152027 A1 | 9/2014 |
| WO | WO 2014/144711 A1 | | 9/2014 |
| WO | WO 2014/152030 A1 | | 9/2014 |
| WO | WO 2014/152659 A1 | | 9/2014 |
| WO | | 2014/159813 A1 | 10/2014 |
| WO | WO 2015/085318 A2 | | 6/2015 |
| WO | | 2015/164773 A1 | 10/2015 |
| WO | WO 2015/188933 A1 | | 12/2015 |
| WO | | 2016/164762 A1 | 10/2016 |
| WO | | 2016/201377 A1 | 12/2016 |
| WO | | 2017/011773 A2 | 1/2017 |
| WO | | 2017/015457 A1 | 1/2017 |
| WO | WO 2017/053297 A1 | | 3/2017 |
| WO | | 2017/066789 A1 | 4/2017 |
| WO | | 2017/070601 A1 | 4/2017 |
| WO | | 2017/098468 A1 | 6/2017 |
| WO | | 2017/112865 A1 | 6/2017 |
| WO | | 2017/127750 A1 | 7/2017 |
| WO | | 2017/201333 A1 | 11/2017 |
| WO | WO 2018/157009 A1 | | 8/2018 |
| WO | WO 2018/157141 A1 | | 8/2018 |
| WO | WO 2019/005540 A1 | | 1/2019 |
| WO | WO 2019/018765 A1 | | 1/2019 |
| WO | WO 2019/036683 A1 | | 2/2019 |
| WO | WO 2020/146814 A1 | | 7/2020 |
| WO | WO 2020/165158 A1 | | 8/2020 |
| WO | WO 2020/190750 A1 | | 9/2020 |
| WO | WO 2020/232371 A1 | | 11/2020 |
| WO | WO 2020/243561 A1 | | 12/2020 |
| WO | WO 2021/030533 A1 | | 2/2021 |
| WO | WO 2021/050864 A1 | | 3/2021 |
| WO | WO 2021/055811 A1 | | 3/2021 |
| WO | WO 2021/055849 A1 | | 3/2021 |
| WO | WO 2021/155243 A1 | | 8/2021 |
| WO | WO 2021/155274 A1 | | 8/2021 |
| WO | WO 2021/159040 A2 | | 8/2021 |
| WO | WO 2021/159130 A2 | | 8/2021 |
| WO | WO 2021/211343 A1 | | 10/2021 |
| WO | WO 2021/222304 A1 | | 11/2021 |
| WO | WO 2021/231929 A1 | | 11/2021 |
| WO | WO 2021/231963 A1 | | 11/2021 |
| WO | WO 2021/237084 A1 | | 11/2021 |
| WO | WO 2021/247817 A1 | | 12/2021 |
| WO | WO 2022/032154 A2 | | 2/2022 |
| WO | WO 2020/061367 A1 | | 3/2022 |
| WO | WO 2022/067010 A1 | | 3/2022 |
| WO | WO 2022/155524 A1 | | 7/2022 |
| WO | WO 2022/155530 A1 | | 8/2022 |
| WO | WO 2022/162027 A2 | | 8/2022 |
| WO | WO 2022/187698 A1 | | 9/2022 |
| WO | WO 2022/197624 A1 | | 9/2022 |
| WO | WO 2022/204491 A1 | | 9/2022 |
| WO | WO 2022/212191 A1 | | 10/2022 |
| WO | WO 2022/212442 A1 | | 10/2022 |
| WO | WO 2022/212711 A1 | | 10/2022 |
| WO | WO 2022/221335 A1 | | 10/2022 |
| WO | WO 2022/221336 A1 | | 10/2022 |
| WO | WO 2022/221359 A1 | | 10/2022 |
| WO | WO 2022/221440 A1 | | 10/2022 |
| WO | WO 2022/226277 A1 | | 10/2022 |
| WO | WO 2022/226318 A1 | | 10/2022 |
| WO | WO 2022/232585 A1 | | 11/2022 |
| WO | WO 2022/241103 A1 | | 11/2022 |
| WO | WO 2022/245888 A1 | | 11/2022 |
| WO | WO 2022/266010 A1 | | 12/2022 |
| WO | WO 2022/266012 A1 | | 12/2022 |
| WO | WO 2022/266389 A1 | | 12/2022 |
| WO | WO 2023/283642 A1 | | 1/2023 |
| WO | WO 2023/283645 A1 | | 1/2023 |
| WO | WO 2023/283651 A1 | | 1/2023 |
| WO | WO 2023/014649 A1 | | 2/2023 |
| WO | WO 2023/018773 A1 | | 2/2023 |
| WO | WO 2023/018923 A1 | | 2/2023 |
| WO | WO 2023/019181 A1 | | 2/2023 |
| WO | WO 2023/056401 A1 | | 4/2023 |
| WO | WO 2023/069625 A1 | | 4/2023 |
| WO | WO 2023/069895 A1 | | 4/2023 |
| WO | WO 2023/069900 A1 | | 4/2023 |
| WO | WO 2023/076358 A1 | | 5/2023 |
| WO | WO 2023/076658 A1 | | 5/2023 |
| WO | WO 2023/081311 A1 | | 5/2023 |
| WO | WO 2023/092069 A1 | | 5/2023 |
| WO | WO 2023/107999 A2 | | 6/2023 |
| WO | WO 2023/114307 A1 | | 6/2023 |
| WO | WO 2023/132885 A1 | | 7/2023 |
| WO | WO 2023/137149 A1 | | 7/2023 |
| WO | WO 2023/150256 A1 | | 8/2023 |
| WO | WO 2023/154818 A1 | | 8/2023 |
| WO | WO 2023/196914 A1 | | 10/2023 |
| WO | WO 2023/201294 A1 | | 10/2023 |
| WO | WO 2023/201296 A1 | | 10/2023 |
| WO | WO 2023/212696 A1 | | 11/2023 |
| WO | WO 2023/225524 A1 | | 11/2023 |
| WO | WO 2023/250119 A1 | | 12/2023 |
| WO | WO 2024/010993 A1 | | 1/2024 |
| WO | WO 2024/015890 A1 | | 1/2024 |
| WO | WO 2024/026005 A1 | | 2/2024 |
| WO | WO 2024/030369 A1 | | 2/2024 |
| WO | WO 2024/050483 A1 | | 3/2024 |
| WO | WO 2024/097874 A1 | | 5/2024 |
| WO | WO 2024/123978 A1 | | 6/2024 |
| WO | WO 2024/151811 A1 | | 7/2024 |
| WO | WO 2024/163465 A1 | | 8/2024 |
| WO | WO 2024/191860 A2 | | 9/2024 |
| WO | WO 2024/206835 A1 | | 10/2024 |
| WO | WO 2024/215721 A1 | | 10/2024 |
| WO | WO 2024/263826 A1 | | 12/2024 |
| WO | WO 2025/019352 A1 | | 1/2025 |

OTHER PUBLICATIONS

Nomura et al., Real-Time Monitoring of in vitro Transcriptional RNA by Using Fluorescence Correlation Spectroscopy. ChemBioChem. Dec. 3, 2004;5(12):1701-1703.

Sei-Lida et al., Real-time monitoring of in vitro transcriptional RNA synthesis using fluorescence resonance energy transfer. Nucleic Acids Res. Jun. 15, 2000;28(12):E59. doi: 10.1093/nar/28.12.e59.

Kang et al., Transcription reinitiation by recycling RNA polymerase that diffuses on DNA after releasing terminated RNA. Nat Commun. Jan. 23, 2020;11(1):450. doi: 10.1038/s41467-019-14200-3.

Kis et al., Stability Modelling of mRNA Vaccine Quality Based on Temperature Monitoring throughout the Distribution Chain. Pharmaceutics. Feb. 17, 2022;14(2):430. doi: 10.3390/pharmaceutics 14020430.

Koubek et al., Strong anion-exchange fast performance liquid chromatography as a versatile tool for preparation and purification of RNA produced by in vitro transcription. RNA. Oct. 2013; 19(10):1449-59. doi: 10.1261/rna.038117.113. Epub Aug. 8, 2013.

Mellits, K.H. et al., Removal of double-stranded contaminants from RNA transcripts: synthesis of adenovirus VA RNAI from a T7 vector. Nucleic Acids Res. Sep. 25, 1990;18(18):5401-6.

Mignone, F. et al., Untranslated regions of mRNAs. Genome Biol. 2002;3(3):REVIEWS0004. Epub Feb. 2, 20028. pp. 1-10.

(56) References Cited

OTHER PUBLICATIONS

Singh et al., Protein Engineering Approaches in the Post-Genomic Era. Curr Protein Pept Sci. 2018;19(1):5-15. doi: 10.2174/1389203718666161117114243.

Yang et al., High performance DNA purification using a novel ion exchange matrix. J Biomol Tech. Jul. 2008;19(3):205-10.

Zhang et al., Propagated Perturbations from a Peripheral Mutation Show Interactions Supporting WW Domain Thermostability. Structure. Nov. 6, 2018;26(11): 1474-1485.e5. doi: 10.1016/j.str.2018.07.014. Epub Sep. 6, 2018.

Schneider et al., Measuring control of transcription initiation by changing concentrations of nucleotides and their derivatives. Methods Enzymol. 2003:370:606-17. doi: 10.1016/S0076-6879(03)70051-2.

Wang et al., Recent advances in mRNA cancer vaccines: meeting challenges and embracing opportunities. Front Immunol. Sep. 6, 2023;14:1246682. doi: 10.3389/fimmu.2023.1246682.

METHODS OF MONITORING IN VITRO TRANSCRIPTION OF mRNA AND/OR POST-IN VITRO TRANSCRIPTION PROCESSES

RELATED APPLICATIONS

This application is a national stage filing under 35 U.S.C. § 371 of international PCT Application PCT/US2022/028969, filed May 12, 2022, which claims priority under 35 U.S.C. § 119(e) to U.S. Provisional Patent Application No. 63/188,583, filed May 14, 2021, the contents of each of which are hereby incorporated herein by reference in their entireties.

FIELD OF INVENTION

The present disclosures relate generally to methods of monitoring in vitro transcription of mRNA and/or post-in vitro transcription processes (e.g., by acquiring one or more Raman spectra during in vitro transcription of mRNA).

BACKGROUND

The use of messenger RNA (mRNA) as a pharmaceutical agent is of great interest for a variety of applications, including in therapeutics, vaccines, and diagnostics. mRNA may be produced by in vitro transcription. However, productivity of in vitro transcription of mRNA represents a continuing challenge, as in vitro transcription of mRNA may be sensitive to small changes in conditions. Without effective means to monitor in vitro transcription of mRNA, changes in conditions and/or low productivity may go undetected, resulting in low yields and/or efficiency, and insufficient mRNA to satisfy needs (e.g., expected patient doses). Accordingly, improved methods of monitoring in vitro transcription of mRNA are desirable.

SUMMARY OF THE INVENTION

The present invention provides, among other things, methods of monitoring in vitro transcription of mRNA and/or post-in vitro transcription processes. The invention encompasses, in some aspects, methods of monitoring in vitro transcription of mRNA by acquiring one or more Raman spectra during in vitro transcription of mRNA in order to increase productivity by, for example, earlier identification and/or modification of undesired reaction conditions, efficient stopping of reactions, and/or optimization of reaction conditions.

According to some aspects, methods are provided herein.

In some embodiments, the method comprises acquiring one or more Raman spectra during in vitro transcription of mRNA. In certain embodiments, the method comprises acquiring one or more Raman spectra during a post-in vitro transcription process. In accordance with certain embodiments, the method comprises using greater than or equal to 1 probe for Raman spectroscopy and less than or equal to 10 probes for Raman spectroscopy.

In certain embodiments, the method further comprises performing in vitro transcription of mRNA. According to some embodiments, the in vitro mRNA transcription comprises a batch process, a fed-batch process, and/or a continuous process.

According to certain embodiments, the method further comprises monitoring one or more reaction conditions and/or progression of the in vitro transcription. In some embodiments, the monitoring comprises monitoring whether all desired components of the in vitro transcription are present, monitoring formation of one or more byproducts, monitoring formation of orthophosphate, monitoring reduction in concentration of one or more reactants, monitoring reduction in concentration of one or more nucleoside triphosphates (NTPs), monitoring one or more full Raman spectra, monitoring one or more peaks of one or more Raman spectra, monitoring a peak representative of mRNA, monitoring one or more peaks at greater than or equal to 970 $cm^{-1}$ and less than or equal to 1000 $cm^{-1}$ of one or more Raman spectra, monitoring one or more peaks at greater than or equal to 1100 $cm^{-1}$ and less than or equal to 1120 $cm^{-1}$ of one or more Raman spectra, monitoring one or more peaks at greater than or equal to 1150 $cm^{-1}$ and less than or equal to 1650 $cm^{-1}$ of one or more Raman spectra, monitoring one or more peaks at greater than or equal to 800 $cm^{-1}$ and less than or equal to 880 $cm^{-1}$ of one or more Raman spectra, monitoring one or more peaks at greater than or equal to 920 $cm^{-1}$ and less than or equal to 940 $cm^{-1}$ of one or more Raman spectra, and/or monitoring one or more peaks at greater than or equal to 1040 $cm^{-1}$ and less than or equal to 1070 $cm^{-1}$ of one or more Raman spectra.

In certain embodiments, the monitoring comprises using an algorithm to determine whether the in vitro transcription has reached a desired endpoint, whether the in vitro transcription is progressing at a desired rate, and/or whether one or more reaction conditions are as desired. According to some embodiments, the algorithm comprises Principal Component Analysis (PCA) and/or a Batch Evolution Model.

In accordance with certain embodiments, the monitoring comprises comparing one or more Raman spectra and/or representations thereof to one or more reference Raman spectra and/or representations thereof to identify the presence of one or more differences. In some embodiments, the method further comprises identifying the cause of the one or more differences that are present.

In accordance with some embodiments, the method further comprises determining whether the in vitro transcription has reached a desired endpoint, whether the in vitro transcription is progressing at a desired rate, and/or whether one or more reaction conditions are as desired.

In some embodiments, the method further comprises optimizing one or more reaction conditions of a subsequent batch of in vitro transcription based on data generated from the monitoring step. In accordance with certain embodiments, the method further comprises modifying one or more reaction conditions after the determining step. In some embodiments, the modifying one or more reaction conditions increases rate of reaction, increases yield, and/or reduces mRNA degradation.

According to certain embodiments, the one or more reaction conditions comprises temperature, concentration of one or more reactants, concentration of one or more components of one or more enzyme solutions, concentration of one or more components of one or more buffer solutions, and/or rate of mixing.

In some embodiments, the method further comprises stopping the in vitro transcription after the determining step.

In certain embodiments, the method further comprises performing and/or monitoring one or more post-in vitro transcription processes. According to some embodiments, the method comprises performing and monitoring one or more post-in vitro transcription processes, wherein the monitoring one or more post-in vitro transcription processes comprises monitoring the presence and/or concentration of one or more components of in vitro transcription during the post-in vitro transcription process.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
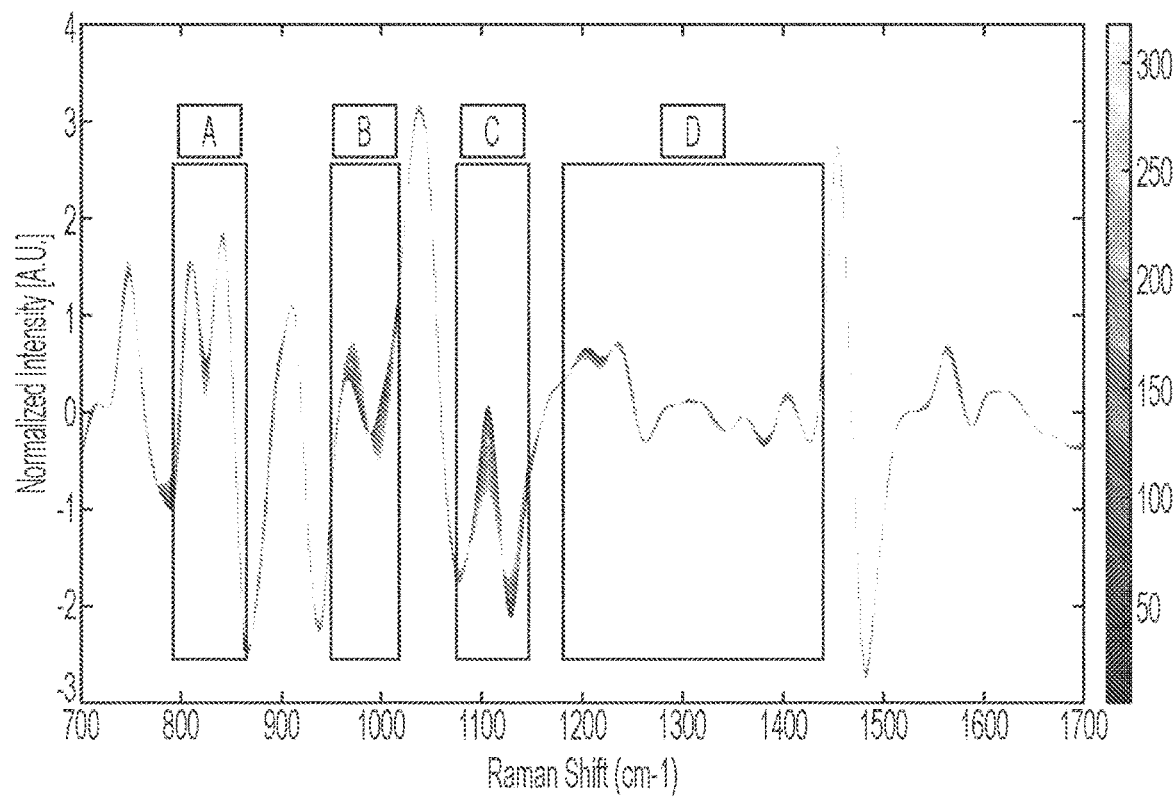
FIG. 1A shows Raman spectra (plotting normalized intensity (AU) versus Raman shift ($cm^{-1}$)) of in vitro transcription of mRNA with gray-scale to show time (with black being the first spectrum and white being the last spectrum). Box A represents peak(s) associated with glycerol, box B represents peak(s) associated with orthophosphate (which is representative of total mRNA), box C represents peak(s) associated with total nucleoside triphosphates (NTPs), and box D represents peak(s) associated with individual NTPs.

The use of messenger RNA (mRNA) as a pharmaceutical agent is of great interest for a variety of applications, including in therapeutics, vaccines, and diagnostics. mRNA may be produced by in vitro transcription. However, productivity of in vitro transcription of mRNA represents a continuing challenge, as in vitro transcription of mRNA may be sensitive to small changes in conditions. Without effective means to monitor in vitro transcription of mRNA, changes in reaction conditions, yield, and/or rate of reaction may go undetected, resulting in low productivity and/or insufficient mRNA to satisfy needs (e.g., expected patient doses). For example, in some cases, having even 1 g/mL mRNA below a target productivity in a batch could result in the delay of 200,000 patient doses. This delay can have significant consequences. For example, in a pandemic, vaccines may be needed almost as, or more, quickly than they can be produced. Accordingly, delays in mRNA production can have significant consequences, as they can result in extension of the time periods for restrictions, such as social distancing requirements, mask requirements, work-from-home requirements, and social gathering size restrictions, as well as in increased illness, hospitalization, and even death compared to earlier vaccination. Accordingly, rapid methods of monitoring changes in reaction conditions, yield, and/or rate of reaction, such that the conditions can be modified (e.g., in batch, fed-batch, and/or continuous processes) or the batch can be ended, are needed.

In some embodiments, the methods disclosed herein provide advantages such as real-time monitoring, rapid detection of undesirable conditions, increased consistency in production, reduced degradation of the mRNA, increased throughput, increased yield, improved cost efficiency, reduction in time spent on low-producing batches, optimization of methods, increased productivity, and/or reduction in manufacturing delays.

Accordingly, provided herein are methods. In some embodiments, the method comprises acquiring one or more Raman spectra during in vitro transcription (IVT) of mRNA.

In certain embodiments, the method comprises performing in vitro transcription of mRNA. In some embodiments, the method comprises performing in vitro transcription of mRNA for a suitable amount of time. For example, in certain embodiments, the method comprises performing in vitro transcription of mRNA for greater than or equal to 60 minutes, greater than or equal to 75 minutes, greater than or equal to 90 minutes, greater than or equal to 105 minutes, greater than or equal to 120 minutes, greater than or equal to 150 minutes, greater than or equal to 180 minutes, greater than or equal to 210 minutes, greater than or equal to 240 minutes, greater than or equal to 270 minutes, greater than or equal to 300 minutes, greater than or equal to 330 minutes, greater than or equal to 360 minutes, greater than or equal to 390 minutes, greater than or equal to 420 minutes, greater than or equal to 450 minutes, greater than or equal to 480 minutes, greater than or equal to 510 minutes, greater than or equal to 540 minutes, greater than or equal to 570 minutes, greater than or equal to 600 minutes, greater than or equal to 630 minutes, greater than or equal to 660 minutes, greater than or equal to 690 minutes, greater than or equal to 720 minutes, greater than or equal to 750 minutes, greater than or equal to 780 minutes, greater than or equal to 810 minutes, greater than or equal to 840 minutes, greater than or equal to 870 minutes, greater than or equal to 900 minutes, greater than or equal to 930 minutes, or greater than or equal to 960 minutes. In some embodiments, the method comprises performing in vitro transcription of mRNA for less than or equal to 1000 minutes, less than or equal to 950 minutes, less than or equal to 900 minutes, less than or equal to 850 minutes, less than or equal to 800 minutes, less than or equal to 750 minutes, less than or equal to 700 minutes, less than or equal to 650 minutes, less than or equal to 600 minutes, less than or equal to 550 minutes, less than or equal to 500 minutes, less than or equal to 450 minutes, less than or equal to 400 minutes, less than or equal to 350 minutes, less than or equal to 300 minutes, less than or equal to 250 minutes, less than or equal to 200 minutes, less than or equal to 150 minutes, or less than or equal to 100 minutes. Combinations of these ranges are also possible (e.g., greater than or equal to 60 minutes and less than or equal to 1000 minutes, greater than or equal to 60 minutes and less than or equal to 600 minutes, greater than or equal to 90 minutes and less than or equal to 600 minutes, greater than or equal to 120 minutes and less than or equal to 500 minutes, greater than or equal to 390 minutes and less than or equal to 600 minutes, greater than or equal to 600 minutes and less than or equal to 1000 minutes, or greater than or equal to 720 minutes and less than or equal to 950 minutes).

According to some embodiments, the method comprises acquiring one or more Raman spectra. In certain embodiments, the methods comprise monitoring in vitro transcription of mRNA (e.g., by acquiring one or more Raman spectra during in vitro transcription of mRNA) and/or a post-in vitro transcription process (e.g., by acquiring one or more Raman spectra during a post-in vitro transcription process). In some embodiments, the methods further comprise making a determination (e.g., based off of the monitoring), such as determining whether the in vitro transcription and/or post-in vitro transcription process has reached a desired endpoint, whether the in vitro transcription and/or post-in vitro transcription progress is progressing at a desired rate, and/or whether one or more reaction conditions (e.g., of in vitro transcription) are as desired. In certain embodiments, the methods further comprise taking an action (e.g., based off of the determination and/or monitoring), such as modifying one or more reaction conditions and/or stopping the in vitro transcription (e.g., before or after it would have been stopped absent the determination and/or monitoring) and/or the post-in vitro transcription progress (e.g., before or after it would have been stopped absent the determination and/or monitoring). Some embodiments comprise continuing to run the in vitro transcription and/or post-in vitro transcription process (e.g., to the endpoint) based off of the determination and/or monitoring. According to some embodiments, the methods further comprise starting a new batch of in vitro transcription.

In some embodiments, monitoring comprises monitoring one or more reaction conditions of the in vitro transcription. Examples of reaction conditions that are monitored in certain embodiments include presence of one or more (e.g., all) of the desired components of in vitro transcription, temperature, concentration of one or more reactants, rate of mixing, concentration of one or more components of one or more enzyme solutions, and/or concentration of one or more components of one or more buffer solutions.

According to some embodiments, the method comprises monitoring the presence of one or more (e.g., all) of the desired components of in vitro transcription (e.g., before the in vitro transcription begins) (e.g., in a batch). In certain embodiments, the method comprises monitoring the wavenumber (e.g., shift in wavenumber) of the largest peak (e.g., the peak with the largest intensity and/or normalized intensity). According to certain embodiments, the wavenumber of the largest peak is monitored as one or more (e.g., all) components are added (e.g., individually or all at once) for in vitro transcription. In some such embodiments, the wavenumber of the largest peak shifts (e.g., the wavenumber of the peak itself may shift or the largest peak may become a different peak as components are added and new peaks grow in size replacing the former largest peak as the new largest peak) as one or more (e.g., all) components is added for in vitro transcription. In some such embodiments, the wavenumber of the largest peak is monitored (e.g., before the in vitro transcription begins) to monitor whether one or more (e.g., all) of the desired components of in vitro transcription are present.

In some embodiments, the method comprises determining that one or more (e.g., all) of the desired components of the in vitro transcription are present (e.g., in a batch). In some such embodiments, the method further comprises beginning in vitro transcription (e.g., of the batch) (e.g., after determining that one or more (e.g., all) of the desired components of the in vitro transcription are present).

In certain embodiments, the method comprises determining that one or more of the desired components of the in vitro transcription are not present (e.g., in a batch). In some such embodiments, the method further comprises adding the component that is not present (e.g., in the batch), making the determination not to begin in vitro transcription with the batch, and/or making the determination to start a new in vitro transcription batch (e.g., after determining that one or more (e.g., all) of the desired components of the in vitro transcription are present). Without wishing to be bound by theory, it is believed that monitoring whether one or more (e.g., all) of the desired components of the in vitro transcription are present (e.g., in a batch) before in vitro transcription begins increases throughput and/or increases yield.

In certain embodiments, the method comprises monitoring the temperature (i.e., the temperature during in vitro transcription). Some embodiments comprise stopping the IVT reaction, modifying the IVT reaction, or proceeding with the IVT reaction based on the monitored temperature and/or Raman spectra.

In some embodiments, the method comprises determining that the in vitro transcription is occurring at the desired temperature. In some embodiments, the desired temperature is greater than or equal to $25°$ C. greater than or equal to $26°$ C., greater than or equal to $27°$ ° C., greater than or equal to $28°$ C., greater than or equal to $29°$ C., greater than or equal to $30°$ C., greater than or equal to $31°$ C., greater than or equal to $32°$ C., greater than or equal to $33°$ C., greater than or equal to $34°$ C., greater than or equal to $35°$ C., greater than or equal to $36°$ C., or greater than or equal to $37°$ C. In accordance with certain embodiments, the desired temperature is less than or equal to $41°$ C., less than or equal to $40°$ C., less than or equal to $39°$ C., less than or equal to $38°$ C., less than or equal to $37°$ C., less than or equal to $36°$ C., less than or equal to $35°$ C., less than or equal to $34°$ C., less than or equal to $33°$ C., less than or equal to $32°$ C., less than or equal to $31°$ C., or less than or equal to $30°$ C. Combinations of these ranges are also possible (e.g., greater than or equal to $25°$ C. and less than or equal to $41°$ C., greater than or equal to $29°$ C. and less than or equal to $39°$ C., or greater than or equal to $36°$ C. and less than or equal to $38°$ C.). In some embodiments, the desired temperature is $37°$ C.

According to some embodiments, the method comprises determining that the in vitro transcription is occurring at a temperature below a desired temperature. For example, in some embodiments, the method comprises determining that the in vitro transcription is occurring at a temperature greater than or equal to $0.1°$ C., greater than or equal to $1°$ C., greater than or equal to $2°$ C., greater than or equal to $3°$ C., greater than or equal to $4°$ C., greater than or equal to $5°$ C. greater than or equal to $7°$ ° C., or greater than or equal to $10°$ C. below a desired temperature (e.g., $37°$)° ° C. In certain embodiments, the method comprises determining that the in vitro transcription is occurring at a temperature less than or equal to $20°$ C., less than or equal to $15°$ C., less than or equal to $10°$ C., less than or equal to $5°$ C., less than or equal to $4°$ C., less than or equal to $3°$ C., less than or equal to $2°$ C., or less than or equal to $1°$ C. below a desired temperature (e.g., $37$)° ° C. Combinations of these ranges are also possible (e.g., greater than or equal to $0.1°$ C. and less than or equal to $20°$ C., greater than or equal to $1°$ C. and less than or equal to $10°$ C., or greater than or equal to $1°$ C. and less than or equal to $3°$ C.).

In accordance with some embodiments, the method comprises determining that the in vitro transcription is occurring at a temperature above a desired temperature. For example, in certain embodiments, the method comprises determining that the in vitro transcription is occurring at a temperature greater than or equal to $0.1°$ C., greater than or equal to $1°$ C., greater than or equal to $2°$ C., greater than or equal to $3°$ ° C., greater than or equal to $4°$ C., greater than or equal to $5°$ C., greater than or equal to $7°$ C., or greater than or equal to $10°$ C. above a desired temperature (e.g., $37$)° ° C. In certain embodiments, the method comprises determining that the in vitro transcription is occurring at a temperature less than or equal to $20°$ C., less than or equal to $15°$ C., less than or equal to $10°$ C., less than or equal to $5°$ C., less than or equal to $4°$ C., less than or equal to $3°$ C., less than or equal to $2°$ C., or less than or equal to $1°$ C. above a desired temperature (e.g., $37$)° ° C. Combinations of these ranges are also possible (e.g., greater than or equal to $0.1°$ C. and less than or equal to $20°$ C., greater than or equal to $1°$ C. and less than or equal to $10°$ C., or greater than or equal to $1°$ C. and less than or equal to $3°$ C.).

According to certain embodiments, the method comprises modifying (e.g., increasing and/or decreasing) the temperature (e.g., after a determination, for example regarding temperature, has been made). For example, in embodiments where the method comprises determining that in vitro transcription is occurring at a temperature below a desired temperature, in some cases, the method comprises increasing the temperature of the in vitro transcription (e.g., to the desired temperature). As another example, in embodiments where the method comprises determining that the in vitro transcription is occurring at a temperature above a desired temperature, in some instances, the method comprises decreasing the temperature of the in vitro transcription (e.g., to the desired temperature).

In accordance with some embodiments, the method comprises stopping the in vitro transcription (e.g., after a determination, for example regarding temperature, has been made).

For example, in embodiments where the method comprises determining that in vitro transcription is occurring at a temperature below a desired temperature, in some cases, the method comprises stopping the in vitro transcription. In some embodiments, the stopping step occurs before the in vitro transcription would have been stopped absent the determination and/or monitoring in cases where the in vitro transcription is occurring at a temperature below a desired temperature. Without wishing to be bound by theory, it is believed that in vitro transcription occurring at a temperature below the desired temperature reduces the rate of reaction and/or increases the time required to reach the endpoint, in certain embodiments, such that stopping the in vitro transcription early reduces time spent on a slow batch, and allows a new faster batch to be started instead. In certain embodiments, the stopping step occurs after the in vitro transcription would have been stopped absent the determination and/or monitoring in cases where the in vitro transcription is occurring at a temperature below a desired temperature. Without wishing to be bound by theory, it is believed that the in vitro transcription occurring at a temperature below the desired temperature reduces the rate of reaction, in certain embodiments, such that stopping the in vitro transcription later increases the yield (e.g., by allowing the reaction additional time to reach its endpoint).

As another example, in embodiments where the method comprises determining that in vitro transcription is occurring at a temperature above a desired temperature, in some cases, the method comprises stopping the in vitro transcription. In some embodiments, the stopping step occurs before the in vitro transcription would have been stopped absent the determination and/or monitoring in cases where the in vitro transcription is occurring at a temperature above a desired temperature. Without wishing to be bound by theory, it is believed that the in vitro transcription occurring at a temperature above the desired temperature increases the rate of reaction, decreases the time required to reach the endpoint, and/or increases the rate of degradation of the mRNA that is formed, in certain embodiments, such that stopping the in vitro transcription early increases throughput (e.g., by stopping the batch when it has reached its endpoint rather than stopping it at the time when it would have reached its endpoint had it been at the desired temperature, and starting a new batch earlier) and/or reduced mRNA degradation (e.g., by reducing the amount of time the mRNA spends at an elevated temperature).

In certain embodiments, the method comprises monitoring the concentration of one or more reactants. In some embodiments the one or more reactants comprises a nucleoside triphosphate (NTP), such as adenosine triphosphate (ATP), guanosine triphosphate (GTP), cytidine triphosphate (CTP), and/or uridine triphosphate (UTP). Some embodiments comprise stopping the IVT reaction, modifying the IVT reaction, or proceeding with the IVT reaction based on the monitored concentration of one or more reactants and/or Raman spectra.

In some embodiments, monitoring the concentration of one or more reactants comprises monitoring the total concentration of the one or more reactants (e.g., the concentration of all NTPS) and/or the concentration of one or more reactants individually (e.g., ATP, GTP, CTP, and/or UTP individually). In certain embodiments, monitoring the concentration of one or more reactants comprises monitoring the absolute concentration of the one or more reactants.

According to some embodiments, monitoring the concentration of one or more reactants comprising monitoring the relative concentration of one or more reactants (e.g., compared to the concentration of one or more other reactants, the concentration of one or more components of an enzyme solution, and/or concentration of one or more components of a buffer solution). For example, in accordance with certain embodiments, monitoring the concentration of one or more reactants comprises monitoring the amount of one NTP relative to another.

In accordance with some embodiments, the method comprises determining that one or more reactants (e.g., as a total and/or individually) (e.g., NTPs, such as ATP, GTP, CTP, and/or UTP) are present at the desired concentration (e.g., desired absolute concentration and/or desired relative concentration, for example for one NTP relative to another).

According to certain embodiments, the method comprises determining that one or more reactants (e.g., as a total and/or individually) (e.g., NTPs, such as ATP, GTP, CTP, and/or UTP) are present at a concentration lower than a desired concentration (e.g., at that timepoint). For example, in some embodiments, the method comprises determining that one or more reactants (e.g., as a total and/or individually) (e.g., NTPs, such as ATP, GTP, CTP, and/or UTP) are present at a concentration greater than or equal to 0.1%, greater than or equal to 1%, greater than or equal to 2%, greater than or equal to 3%, greater than or equal to 4%, greater than or equal to 5%, greater than or equal to 10%, greater than or equal to 15%, greater than or equal to 20%, greater than or equal to 25%, or greater than or equal to 30% lower than a desired concentration (e.g., at that timepoint). In certain embodiments, the method comprises determining that one or more reactants (e.g., as a total and/or individually) (e.g., NTPs, such as ATP, GTP, CTP, and/or UTP) are present at a concentration less than or equal to 100%, less than or equal to 90%, less than or equal to 75%, less than or equal to 50%, less than or equal to 40%, less than or equal to 30%, less than or equal to 25%, less than or equal to 20%, less than or equal to 15%, less than or equal to 10%, less than or equal to 5%, or less than or equal to 3% lower than a desired concentration (e.g., at that timepoint). Combinations of these ranges are also possible (e.g., greater than or equal to 0.1% and less than or equal to 100%, greater than or equal to 1% and less than or equal to 50%, greater than or equal to 10% and less than or equal to 40%, or greater than or equal to 15% and less than or equal to 25%). In certain embodiments, the method comprises determining that one or more reactants (e.g., as a total and/or individually) (e.g., NTPs, such as ATP, GTP, CTP, and/or UTP) are absent.

According to certain embodiments, the method comprises determining that one or more reactants (e.g., as a total and/or individually) (e.g., NTPs, such as ATP, GTP, CTP, and/or UTP) are present at a concentration higher than a desired concentration (e.g., at that timepoint). For example, in some embodiments, the method comprises determining that one or more reactants (e.g., as a total and/or individually) (e.g., NTPs, such as ATP, GTP, CTP, and/or UTP) are present at a concentration greater than or equal to 0.1%, greater than or equal to 1%, greater than or equal to 2%, greater than or equal to 3%, greater than or equal to 4%, greater than or equal to 5%, greater than or equal to 10%, greater than or equal to 15%, greater than or equal to 20%, greater than or equal to 25%, or greater than or equal to 30% higher than a desired concentration (e.g., at that timepoint). In certain embodiments, the method comprises determining that one or more reactants (e.g., as a total and/or individually) (e.g., NTPs, such as ATP, GTP, CTP, and/or UTP) are present at a concentration less than or equal to 100%, less than or equal to 90%, less than or equal to 75%, less than or equal to 50%, less than or equal to 40%, less than or equal to 30%, less than or equal to 25%, less than or equal to 20%, less than or equal to 15%, less than or equal to 10%, less than or equal to 5%, or less than or equal to 3% higher than a desired concentration (e.g., at that timepoint). Combinations of these ranges are also possible (e.g., greater than or equal to 0.1% and less than or equal to 100%, greater than or equal to 1% and less than or equal to 50%, greater than or equal to 10% and less than or equal to 40%, or greater than or equal to 15% and less than or equal to 25%). In certain embodiments, the method comprises determining that one or more reactants are present that should not be present.

According to certain embodiments, the method comprises modifying (e.g., increasing and/or decreasing) the concentration (e.g., after a determination, for example regarding concentration of one or more reactants, has been made) of one or more reactants (e.g., as a total and/or individually) (e.g., NTPs, such as ATP, GTP, CTP, and/or UTP). For example, in embodiments where the method comprises determining that one or more reactants (e.g., as a total and/or individually) (e.g., NTPs, such as ATP, GTP, CTP, and/or UTP) are present at a concentration lower than a desired concentration, in some cases, the method comprises increasing the concentration of that one or more reactants (e.g., to the desired concentration). As another example, in embodiments where the method comprises determining that the one or more reactants (e.g., as a total and/or individually) (e.g., NTPs, such as ATP, GTP, CTP, and/or UTP) are present at a concentration higher than a desired concentration, in some cases, the method comprises decreasing the concentration of that one or more reactants (e.g., to the desired concentration).

In accordance with some embodiments, the method comprises stopping the in vitro transcription (e.g., after a determination, for example regarding the concentration of one or more reactants, has been made). For example, in embodiments where the method comprises determining that one or more reactants (e.g., as a total and/or individually) (e.g., NTPs, such as ATP, GTP, CTP, and/or UTP) are present at a concentration lower than a desired concentration, in some cases, the method comprises stopping the in vitro transcription. In some embodiments, the stopping step occurs before the in vitro transcription would have been stopped absent the determination and/or monitoring in cases where the one or more reactants (e.g., as a total and/or individually) (e.g., NTPs, such as ATP, GTP, CTP, and/or UTP) are present at a concentration lower than a desired concentration. Without wishing to be bound by theory, it is believed that having one or more reactants (e.g., as a total and/or individually) (e.g., NTPs, such as ATP, GTP, CTP, and/or UTP) present at a concentration lower than a desired concentration reduces the rate of reaction, reduces the yield, and/or reduces the time required to reach the endpoint (e.g., as the endpoint is different due to reduced yield), in certain embodiments, such that stopping the in vitro transcription early reduces time spent on a slow batch (allowing a new faster batch to be started instead), reduces time spent on a low yield batch (allowing a new higher yield batch to be started instead), and/or increases throughput (e.g., if there are insufficient reactants, the in vitro transcription may reach its endpoint earlier than expected, such that the batch can be stopped and a new batch can be started). In certain embodiments, the stopping step occurs after the in vitro transcription would have been stopped absent the determination and/or monitoring in cases where the one or more reactants (e.g., as a total and/or individually) (e.g., NTPs, such as ATP, GTP, CTP, and/or UTP) are present at a concentration lower than a desired concentration. Without wishing to be bound by theory, it is believed that having one or more reactants (e.g., as a total and/or individually) (e.g., NTPs, such as ATP, GTP, CTP, and/or UTP) present at a concentration lower than a desired concentration reduces the rate of reaction, reduces the yield, and/or increases the time required to reach the endpoint, in certain embodiments, such that stopping the in vitro transcription later increases the yield (e.g., by allowing the reaction additional time to reach its endpoint).

As another example, in embodiments where the method comprises determining that one or more reactants (e.g., as a total and/or individually) (e.g., NTPs, such as ATP, GTP, CTP, and/or UTP) are present at a concentration higher than a desired concentration, in some cases, the method comprises stopping the in vitro transcription. In some embodiments, the stopping step occurs before the in vitro transcription would have been stopped absent the determination and/or monitoring in cases where the one or more reactants (e.g., as a total and/or individually) (e.g., NTPs, such as ATP, GTP, CTP, and/or UTP) are present at a concentration higher than a desired concentration. Without wishing to be bound by theory, it is believed that having one or more reactants (e.g., as a total and/or individually) (e.g., NTPs, such as ATP, GTP, CTP, and/or UTP) present at a concentration higher than a desired concentration reduces the rate of reaction and/or increases the time required to reach the endpoint (e.g., by inhibiting the reaction), in certain embodiments, such that stopping the in vitro transcription earlier reduces time spent on a slow batch, and allows a new faster batch to be started instead. In certain embodiments, the stopping step occurs after the in vitro transcription would have been stopped absent the determination and/or monitoring in cases where the one or more reactants (e.g., as a total and/or individually) (e.g., NTPs, such as ATP, GTP, CTP, and/or UTP) are present at a concentration higher than a desired concentration. Without wishing to be bound by theory, it is believed that having one or more reactants (e.g., as a total and/or individually) (e.g., NTPs, such as ATP, GTP, CTP, and/or UTP) present at a concentration higher than a desired concentration reduces the rate of reaction and/or increases the time required to reach the endpoint (e.g., by inhibiting the reaction), in certain embodiments, such that stopping the in vitro transcription later increases the yield (e.g., by allowing the reaction additional time to reach its endpoint).

In certain embodiments, the method comprises monitoring concentration(s) of one or more components of an enzyme solution during in vitro transcription of mRNA. Non-limiting examples of suitable components of one or more enzyme solutions include glycerol and/or one or more enzymes. Non-limiting examples of suitable enzymes include an RNA polymerase solution (e.g., a T7 polymerase enzyme solution) and/or a pyrophosphatase solution. In some embodiments, monitoring concentration(s) of one or more components of an enzyme solution allows determination of the concentration of the one or more enzymes. In certain embodiments, monitoring the concentration of the one or more components of an enzyme solution comprises monitoring the absolute concentration of the one or more components. According to some embodiments, monitoring the concentration of the one or more components of an enzyme solution comprises monitoring the relative concentration of the one or more components (e.g., compared to the concentration of one or more other reactants).

In accordance with some embodiments, the method comprises determining that the one or more components of an enzyme solution (e.g., glycerol and/or the enzyme) is present at a desired concentration. Some embodiments comprise stopping the IVT reaction, modifying the IVT reaction, or proceeding with the IVT reaction based on the monitored components and/or Raman spectra.

According to certain embodiments, the method comprises determining that the one or more components of an enzyme solution is present at a concentration lower than a desired concentration. For example, in some embodiments, the method comprises determining that the one or more components of an enzyme solution is present at a concentration greater than or equal to 0.1%, greater than or equal to 1%, greater than or equal to 2%, greater than or equal to 3%, greater than or equal to 4%, greater than or equal to 5%, greater than or equal to 10%, greater than or equal to 15%, greater than or equal to 20%, greater than or equal to 25%, or greater than or equal to 30% lower than a desired concentration. In certain embodiments, the method comprises determining that the one or more components of an enzyme solution is present at a concentration less than or equal to 100%, less than or equal to 90%, less than or equal to 75%, less than or equal to 50%, less than or equal to 40%, less than or equal to 30%, less than or equal to 25%, less than or equal to 20%, less than or equal to 15%, less than or equal to 10%, less than or equal to 5%, or less than or equal to 3% lower than a desired concentration. Combinations of these ranges are also possible (e.g., greater than or equal to 0.1% and less than or equal to 100%, greater than or equal to 1% and less than or equal to 50%, greater than or equal to 10% and less than or equal to 40%, or greater than or equal to 15% and less than or equal to 25%). In certain embodiments, the method comprises determining that the one or more components of an enzyme solution is absent.

According to certain embodiments, the method comprises determining that the one or more components of an enzyme solution is present at a concentration higher than a desired concentration. For example, in some embodiments, the method comprises determining that the one or more components of an enzyme solution is present at a concentration greater than or equal to 0.1%, greater than or equal to 1%, greater than or equal to 2%, greater than or equal to 3%, greater than or equal to 4%, greater than or equal to 5%, greater than or equal to 10%, greater than or equal to 15%, greater than or equal to 20%, greater than or equal to 25%, or greater than or equal to 30% higher than a desired concentration. In certain embodiments, the method comprises determining that the one or more components of an enzyme solution is present at a concentration less than or equal to 100%, less than or equal to 90%, less than or equal to 75%, less than or equal to 50%, less than or equal to 40%, less than or equal to 30%, less than or equal to 25%, less than or equal to 20%, less than or equal to 15%, less than or equal to 10%, less than or equal to 5%, or less than or equal to 3% higher than a desired concentration. Combinations of these ranges are also possible (e.g., greater than or equal to 0.1% and less than or equal to 100%, greater than or equal to 1% and less than or equal to 50%, greater than or equal to 10% and less than or equal to 40%, or greater than or equal to 15% and less than or equal to 25%). In certain embodiments, the method comprises determining that one or more components of an enzyme solution is present that should not be present.

According to certain embodiments, the method comprises modifying (e.g., increasing and/or decreasing) the concentration (e.g., after a determination, for example regarding concentration of the one or more components of an enzyme solution, has been made) of the one or more components of an enzyme solution (e.g., by modifying the concentration of the enzyme solution as a whole). For example, in embodiments where the method comprises determining that the one or more components of an enzyme solution is present at a concentration lower than a desired concentration, in some cases, the method comprises increasing the concentration of the one or more components of the enzyme solution (e.g., to the desired concentration) (e.g., by adding additional enzyme solution). As another example, in embodiments where the method comprises determining that the one or more components of an enzyme solution is present at a concentration higher than a desired concentration, in some cases, the method comprises decreasing the concentration of the one or more components of the enzyme solution (e.g., by decreasing the concentration of the enzyme solution as a whole) (e.g., to the desired concentration).

In accordance with some embodiments, the method comprises stopping the in vitro transcription (e.g., after a determination, for example regarding the concentration of the one or more components of an enzyme solution, has been made). For example, in embodiments where the method comprises determining that the one or more components of an enzyme solution is present at a concentration lower than a desired concentration, in some cases, the method comprises stopping the in vitro transcription. In some embodiments, the stopping step occurs before the in vitro transcription would have been stopped absent the determination and/or monitoring in cases where the one or more components of an enzyme solution is present at a concentration lower than a desired concentration. Without wishing to be bound by theory, it is believed that having one or more components of an enzyme solution present at a concentration lower than a desired concentration reduces the rate of reaction, reduces the yield, and/or increases the time required to reach the endpoint, in certain embodiments, such that stopping the in vitro transcription early reduces time spent on a slow batch (allowing a new faster batch to be started instead). In certain embodiments, the stopping step occurs after the in vitro transcription would have been stopped absent the determination and/or monitoring in cases where the one or more components of an enzyme solution is present at a concentration lower than a desired concentration. Without wishing to be bound by theory, it is believed that having the one or more components of an enzyme solution present at a concentration lower than a desired concentration reduces the rate of reaction, reduces the yield, and/or increases the time required to reach the endpoint, in certain embodiments, such that stopping the in vitro transcription later increases the yield (e.g., by allowing the reaction additional time to reach its endpoint).

As another example, in embodiments where the method comprises determining that the one or more components of an enzyme solution is present at a concentration higher than a desired concentration, in some cases, the method comprises stopping the in vitro transcription. In some embodiments, the stopping step occurs before the in vitro transcription would have been stopped absent the determination and/or monitoring in cases where the one or more components of an enzyme solution is present at a concentration higher than a desired concentration. Without wishing to be bound by theory, it is believed that having the one or more components of an enzyme solution present at a concentration higher than a desired concentration increases the rate of reaction and/or decreases the time required to reach the endpoint, in certain embodiments, such that stopping the in vitro transcription early increases throughput (e.g., by stopping the batch when it has reached its endpoint rather than stopping it at the time when it would have reached its endpoint had it had the desired concentration of one or more components of the enzyme solution, and starting a new batch earlier). In certain embodiments, the stopping step occurs after the in vitro transcription would have been stopped absent the determination and/or monitoring in cases where the one or more components of an enzyme solution is present at a concentration higher than a desired concentration.

In certain embodiments, the method comprises monitoring the rate of mixing during in vitro transcription of mRNA. Some embodiments comprise stopping the IVT reaction, modifying the IVT reaction, or proceeding with the IVT reaction based on the monitored rate of mixing and/or Raman spectra.

In accordance with some embodiments, the method comprises determining that the rate of mixing during in vitro transcription of mRNA is at a desired rate of mixing.

According to certain embodiments, the method comprises determining that the rate of mixing during in vitro transcription of mRNA is lower than a desired rate of mixing. For example, in some embodiments, the method comprises determining that the rate of mixing during in vitro transcription of mRNA is greater than or equal to 1%, greater than or equal to 3%, greater than or equal to 5%, greater than or equal to 10%, greater than or equal to 15%, greater than or equal to 20%, greater than or equal to 25%, greater than or equal to 50%, or greater than or equal to 75% lower than a desired rate of mixing. In certain embodiments, the method comprises determining that the rate of mixing during in vitro transcription of mRNA is less than or equal to 100%, less than or equal to 90%, less than or equal to 75%, less than or equal to 50%, less than or equal to 40%, less than or equal to 30%, less than or equal to 25%, less than or equal to 20%, less than or equal to 15%, less than or equal to 10%, or less than or equal to 5% lower than a desired rate of mixing. Combinations of these ranges are also possible (e.g., greater than or equal to 1% and less than or equal to 100%, greater than or equal to 5% and less than or equal to 50%, greater than or equal to 10% and less than or equal to 30%). In certain embodiments, the method comprises determining that mixing is absent.

According to certain embodiments, the method comprises determining that the rate of mixing during in vitro transcription of mRNA is higher than a desired rate of mixing. For example, in some embodiments, the method comprises determining that the rate of mixing during in vitro transcription of mRNA is greater than or equal to 1%, greater than or equal to 3%, greater than or equal to 5%, greater than or equal to 10%, greater than or equal to 15%, greater than or equal to 20%, greater than or equal to 25%, greater than or equal to 50%, or greater than or equal to 75% higher than a desired rate of mixing. In certain embodiments, the method comprises determining that the rate of mixing during in vitro transcription of mRNA is less than or equal to 100%, less than or equal to 90%, less than or equal to 75%, less than or equal to 50%, less than or equal to 40%, less than or equal to 30%, less than or equal to 25%, less than or equal to 20%, less than or equal to 15%, less than or equal to 10%, or less than or equal to 5% higher than a desired rate of mixing. Combinations of these ranges are also possible (e.g., greater than or equal to 1% and less than or equal to 100%, greater than or equal to 5% and less than or equal to 50%, greater than or equal to 10% and less than or equal to 30%). In certain embodiments, the method comprises determining that mixing is occurring when it should not be occurring.

According to certain embodiments, the method comprises modifying (e.g., increasing and/or decreasing) the rate of mixing (e.g., after a determination, for example regarding rate of mixing, has been made). For example, in embodiments where the method comprises determining that the rate of mixing is lower than a desired rate of mixing, in some cases, the method comprises increasing the rate of mixing (e.g., to the desired rate of mixing). As another example, in embodiments where the method comprises determining that the rate of mixing is higher than a desired rate of mixing, in some cases, the method comprises decreasing the rate of mixing (e.g., to the desired rate of mixing).

In accordance with some embodiments, the method comprises stopping the in vitro transcription (e.g., after a determination, for example regarding the rate of mixing, has been made). For example, in embodiments where the method comprises determining that the rate of mixing is lower than a desired rate of mixing, in some cases, the method comprises stopping the in vitro transcription. In some embodiments, the stopping step occurs before the in vitro transcription would have been stopped absent the determination and/or monitoring in cases where the rate of mixing is lower than a desired rate of mixing. Without wishing to be bound by theory, it is believed that having the rate of mixing lower than a desired rate of mixing reduces the rate of reaction and/or increases the time required to reach the endpoint, in certain embodiments, such that stopping the in vitro transcription early reduces time spent on a slow batch (allowing a new faster batch to be started instead). In certain embodiments, the stopping step occurs after the in vitro transcription would have been stopped absent the determination and/or monitoring in cases where the rate of mixing is lower than a desired concentration. Without wishing to be bound by theory, it is believed that having the rate of mixing lower than a desired rate of mixing reduces the rate of reaction and/or increases the time required to reach the endpoint, in certain embodiments, such that stopping the in vitro transcription later increases the yield (e.g., by allowing the reaction additional time to reach its endpoint).

As another example, in embodiments where the method comprises determining that the rate of mixing is higher than a desired rate of mixing, in some cases, the method comprises stopping the in vitro transcription. In some embodiments, the stopping step occurs before the in vitro transcription would have been stopped absent the determination and/or monitoring in cases where the rate of mixing is higher than a desired rate of mixing. Without wishing to be bound by theory, it is believed that having the rate of mixing higher than a desired rate of mixing reduces the rate of reaction, increases the time required to reach the endpoint, and/or the reduces yield (e.g., by damaging the enzyme), in certain embodiments, such that stopping the in vitro transcription early reduces time spent on a slow and/or low-producing batch. In certain embodiments, the stopping step occurs after the in vitro transcription would have been stopped absent the determination and/or monitoring in cases where the rate of mixing is higher than a desired rate of mixing. Without wishing to be bound by theory, it is believed that having the rate of mixing higher than a desired rate of mixing reduces the rate of reaction and/or increases the time required to reach the endpoint (e.g., by damaging the enzyme), in certain embodiments, such that stopping the in vitro transcription later increases the yield (e.g., by allowing the reaction additional time to reach its endpoint).

In certain embodiments, the method comprises monitoring concentration of one or more components of a buffer solution during in vitro transcription of mRNA. Non-limiting examples of suitable components of one or more buffers, include acetate (e.g., in a magnesium-acetate buffer) and/or tris (e.g., in a tris buffer). In certain embodiments, monitoring the concentration of the one or more components of a buffer solution comprises monitoring the absolute concentration of the one or more components. According to some embodiments, monitoring the concentration of the one or more components of a buffer solution comprises monitoring the relative concentration of the one or more components (e.g., compared to the concentration of one or more other reactants).

In accordance with some embodiments, the method comprises determining that the one or more components of a buffer solution (e.g., acetate and/or tris) is present at a desired concentration. In certain embodiments, the desired concentration of the one or more components of the buffer solution is greater than or equal to 20 mM, greater than or equal to 25 mM, greater than or equal to 30 mM, greater than or equal to 35 mM, greater than or equal to 40 mM, greater than or equal to 45 mM, greater than or equal to 50 mM, or greater than or equal to 55 mM. In some embodiments, the desired concentration of the one or more components of the buffer solution is less than or equal to 60 mM, less than or equal 55 mM, less than or equal to 50 mM, less than or equal 45 mM, less than or equal to 40 mM, less than or equal to 35 mM, less than or equal to 30 mM, or less than or equal 25 mM.

Combinations of these ranges are also possible (e.g., greater than or equal to 20 mM and less than or equal 60 mM).

According to certain embodiments, the method comprises determining that the one or more components of a buffer solution is present at a concentration lower than a desired concentration. For example, in some embodiments, the method comprises determining that the one or more components of a buffer solution is present at a concentration greater than or equal to 0.1%, greater than or equal to 1%, greater than or equal to 2%, greater than or equal to 3%, greater than or equal to 4%, greater than or equal to 5%, greater than or equal to 10%, greater than or equal to 15%, greater than or equal to 20%, greater than or equal to 25%, or greater than or equal to 30% lower than a desired concentration. In certain embodiments, the method comprises determining that the one or more components of a buffer solution is present at a concentration less than or equal to 100%, less than or equal to 90%, less than or equal to 75%, less than or equal to 50%, less than or equal to 40%, less than or equal to 30%, less than or equal to 25%, less than or equal to 20%, less than or equal to 15%, less than or equal to 10%, less than or equal to 5%, or less than or equal to 3% lower than a desired concentration. Combinations of these ranges are also possible (e.g., greater than or equal to 0.1% and less than or equal to 100%, greater than or equal to 1% and less than or equal to 50%, greater than or equal to 10% and less than or equal to 40%, or greater than or equal to 15% and less than or equal to 25%). In certain embodiments, the method comprises determining that the one or more components of a buffer solution is absent.

According to certain embodiments, the method comprises determining that the one or more components of a buffer solution is present at a concentration higher than a desired concentration. For example, in some embodiments, the method comprises determining that the one or more components of a buffer solution is present at a concentration greater than or equal to 0.1%, greater than or equal to 1%, greater than or equal to 2%, greater than or equal to 3%, greater than or equal to 4%, greater than or equal to 5%, greater than or equal to 10%, greater than or equal to 15%, greater than or equal to 20%, greater than or equal to 25%, or greater than or equal to 30% higher than a desired concentration. In certain embodiments, the method comprises determining that the one or more components of a buffer solution is present at a concentration less than or equal to 100%, less than or equal to 90%, less than or equal to 75%, less than or equal to 50%, less than or equal to 40%, less than or equal to 30%, less than or equal to 25%, less than or equal to 20%, less than or equal to 15%, less than or equal to 10%, less than or equal to 5%, or less than or equal to 3% higher than a desired concentration (e.g., at that timepoint). Combinations of these ranges are also possible (e.g., greater than or equal to 0.1% and less than or equal to 100%, greater than or equal to 1% and less than or equal to 50%, greater than or equal to 10% and less than or equal to 40%, or greater than or equal to 15% and less than or equal to 25%). In certain embodiments, the method comprises determining that one or more components of a buffer solution is present that should not be present.

According to certain embodiments, the method comprises modifying (e.g., increasing and/or decreasing) the concentration (e.g., after a determination, for example regarding concentration of the one or more components of a buffer solution, has been made) of the one or more components of a buffer solution (e.g., the buffer solution as a whole). For example, in embodiments where the method comprises determining that the one or more components of a buffer solution is present at a concentration lower than a desired concentration, in some cases, the method comprises increasing the concentration of the one or more components of a buffer solution (e.g., the buffer solution as a whole) (e.g., to the desired concentration). As another example, in embodiments where the method comprises determining that the one or more components of a buffer solution is present at a concentration higher than a desired concentration, in some cases, the method comprises decreasing the concentration of the one or more components of a buffer solution (e.g., the buffer solution as a whole) (e.g., to the desired concentration).

In accordance with some embodiments, the method comprises stopping the in vitro transcription (e.g., after a determination, for example regarding the concentration of the one or more components of a buffer solution, has been made). For example, in embodiments where the method comprises determining that the one or more components of a buffer solution is present at a concentration lower than a desired concentration, in some cases, the method comprises stopping the in vitro transcription. In some embodiments, the stopping step occurs before the in vitro transcription would have been stopped absent the determination and/or monitoring in cases where the one or more components of a buffer solution is present at a concentration lower than a desired concentration. Without wishing to be bound by theory, it is believed that having a concentration of one or more components of a buffer solution lower than a desired concentration reduces the rate of reaction and/or increases the time required to reach the endpoint, in certain embodiments, such that stopping the in vitro transcription early reduces time spent on a slow batch (allowing a new faster batch to be started instead). In certain embodiments, the stopping step occurs after the in vitro transcription would have been stopped absent the determination and/or monitoring in cases where the one or more components of a buffer solution is present at a concentration lower than a desired concentration. Without wishing to be bound by theory, it is believed that having a concentration of one or more components of a buffer solution lower than a desired concentration reduces the rate of reaction and/or increases the time required to reach the endpoint, in certain embodiments, such that stopping the in vitro transcription later increases the yield (e.g., by allowing the reaction additional time to reach its endpoint).

As another example, in embodiments where the method comprises determining that the one or more components of a buffer solution is present at a concentration higher than a desired concentration, in some cases, the method comprises stopping the in vitro transcription. In some embodiments, the stopping step occurs before the in vitro transcription would have been stopped absent the determination and/or monitoring in cases where the one or more components of a buffer solution is present at a concentration higher than a desired concentration. In certain embodiments, the stopping step occurs after the in vitro transcription would have been stopped absent the determination and/or monitoring in cases where the one or more components of a buffer solution is present at a concentration higher than a desired concentration.

In certain embodiments, the method comprises determining that one or more species (e.g., a contaminant) are present that should not be present. For example, the method comprises determining that residual cleaning product (e.g., ethanol) (e.g., used to clean equipment) is present in the in vitro transcription of mRNA, in certain cases. In some embodiments, the method comprises stopping the in vitro transcription (e.g., after a determination, for example regarding the presence of a contaminant, has been made). Some embodiments comprise stopping the IVT reaction, modifying the IVT reaction, or proceeding with the IVT reaction based on the monitored species and/or Raman spectra.

In some embodiments, the method comprises performing and/or monitoring one or more post-in vitro transcription processes. A non-limiting example of a post-in vitro transcription process is Tangential Flow Filtration (TFF). In some embodiments, monitoring one or more post-in vitro transcription processes (e.g., TFF) comprises monitoring the presence and/or concentration of one or more (e.g., all) components of in vitro transcription (such as one or more reactants (e.g., one or more, or total, NTPs), one or more components of one or more enzyme solutions, one or more components of one or more buffer solutions, water, and/or mRNA) during the post-in vitro transcription process.

According to certain embodiments, the method comprises determining that one or more (e.g., all) components of in vitro transcription are no longer present and/or are present at or below the desired concentration upper limit. In some such embodiments, the method comprises stopping the post-in vitro transcription process (e.g., TFF) (e.g., after determining that one or more (e.g., all) components of in vitro transcription are no longer present and/or are present at or below the desired concentration upper limit).

In accordance with some embodiments, the method comprises determining that one or more (e.g., all) components of in vitro transcription are still present and/or are at a higher concentration than desired. In some such embodiments, the method comprises continuing the post-in vitro transcription process (e.g., TFF) after determining that one or more (e.g., all) components of in vitro transcription are still present and/or are present at a higher concentration than desired. For example, in certain embodiments, after determining that one or more (e.g., all) components of in vitro transcription are still present and/or are present at a higher concentration than desired, the method comprises continuing the post-in vitro transcription process (e.g., TFF) until determining that one or more (e.g., all) components of in vitro transcription are no longer present and/or are present at or below the desired concentration upper limit. In certain such embodiments, the method comprises stopping the post-in vitro transcription process (e.g., TFF) (e.g., after determining that one or more (e.g., all) components of in vitro transcription are no longer present and/or are present at or below the desired concentration upper limit). Without being bound by theory, it is believed that monitoring one or more post-in vitro transcription processes (e.g., monitoring the presence and/or concentration of one or more (e.g., all) components of in vitro transcription) increases throughput and/or increases purity (e.g., of the post-in vitro transcription product).

In certain embodiments, monitoring comprises monitoring progression of the in vitro transcription. As a non-limiting example, in some embodiments, the method comprises determining whether the in vitro transcription has reached a desired endpoint and/or whether the in vitro transcription is progressing at a desired rate. Some embodiments comprise stopping the IVT reaction, modifying the IVT reaction, or proceeding with the IVT reaction based on the monitored progression and/or Raman spectra.

As used herein, the endpoint of in vitro transcription is when the levels of mRNA being formed no longer substantially increase (e.g., increase at a rate less than or equal to 5%, less than or equal to 3%, less than or equal to 1%, or less than or equal to 0.1% of the highest rate of reaction observed for that batch of in vitro transcription, or there is no observable increase) over time (e.g., as determined by Raman spectroscopy). For example, in FIG. 1B, the endpoint is represented by box F, as the levels of mRNA (represented by the levels of orthophosphate) being formed are no longer substantially increasing at that point.

As used herein, the rate of reaction (also called "rate" herein) is the change in the level of mRNA over time (e.g., as determined by Raman spectroscopy). For example, the rate of reaction (R) may be determined by the following equation:

$$\text{Rate of Reaction}(R) = (I_2 - I_1)/(T_2 - T_1)$$

where $I_1$ is the intensity (of a peak representative of the total levels of mRNA) at a first timepoint, $I_2$ is the intensity (of the same peak representative of the total levels of mRNA) at a second timepoint (which is later than the first timepoint), $T_1$ is the time at the first timepoint, and $T_2$ is the time at the second timepoint. When the rate of reaction is determined using the equation above, the two timepoints should be selected from a linear portion of the curve with a non-zero slope. For example, the rate of reaction should not be determined at the endpoint (where the slope would be approximately zero) or near the endpoint (where the slope would be non-linear as the rate decreases to zero). A skilled person may determine whether a portion of the curve is linear by performing a linear regression analysis for at least 3 timepoints (e.g., at least 5, at least 7, or at least 9 timepoints; less than or equal to 10, less than or equal to 8, or less than or equal to 6 timepoints; combinations are also possible) and achieving an R-squared value of at least 0.8 (e.g., at least 0.85, at least 0.9, at least 0.95, or at least 0.99; less than or equal to 1, less than or equal to 0.99; less than or equal to 0.99; or less than or equal to 0.95; combinations are also possible, such as at least 0.8 and less than or equal to 1). It should be noted that, as used herein, all references to intensity include normalized intensity.

As discussed elsewhere herein, the change in the levels of mRNA, and, thus, the endpoint and/or rate of reaction, can be determined by observing the change in other species that are directly related to the formation of mRNA (e.g., the decrease in one or more reactants and/or the increase in byproducts, such as orthophosphate), in some embodiments.

In some embodiments, monitoring progression of the in vitro transcription comprises monitoring whether the in vitro transcription has reached a desired endpoint. In certain embodiments, the ability to monitor whether the in vitro transcription has reached a desired endpoint has advantages, including increased yield (e.g., by ensuring that the reaction reaches its endpoint before stopping the batch), improved cost efficiency (e.g., by ensuring that the reaction reaches its endpoint before stopping it, such that reactants are not wasted), and/or increased throughput (e.g., by allowing batches to be stopped as soon as they reach their endpoint, such that new batches may be started) which may increase productivity and/or reduce manufacturing delays.

In accordance with certain embodiments, the method comprises determining that the in vitro transcription has reached the desired endpoint (e.g., which may be before predicted, after predicted, or when predicted, in various embodiments). According to some embodiments, the method comprises stopping the in vitro transcription after it has been determined that the in vitro transcription has reached the desired endpoint. Without wishing to be bound by theory, it is believed that stopping the in vitro transcription once the desired endpoint has been reached increases throughput (e.g., by allowing batches to be stopped as soon as they reach their endpoint, such that new batches may be started), in some embodiments In accordance with some embodiments, the method comprises determining that the in vitro transcription has not yet reached the desired endpoint (e.g., which may be before predicted, after predicted, or when predicted, in various embodiments). According to certain embodiments, the method comprises allowing the in vitro transcription to continue (e.g., until the endpoint is reached) after it has been determined that the in vitro transcription has not yet reached the desired endpoint. Without wishing to be bound by theory, it is believed that allowing the in vitro transcription to continue after it has been determined that the in vitro transcription has not yet reached the desired endpoint increases yield (e.g., by ensuring that the reaction reaches its endpoint before stopping the batch), in certain embodiments.

In certain embodiments where the method comprises allowing the in vitro transcription to continue after it has been determined that the in vitro transcription has not yet reached the desired endpoint, one or more reaction conditions (e.g., temperature, one or more reactant concentrations, concentration of one or more components of an enzyme solution, concentration of one or more components of a buffer solution, and/or rate of mixing) are modified. In some embodiments where the method comprises allowing the in vitro transcription to continue after it has been determined that the in vitro transcription has not yet reached the desired endpoint, no reaction conditions are modified.

In some embodiments, the method comprises stopping the in vitro transcription after it has been determined that the in vitro transcription has not yet reached the desired endpoint.

As another example, in some embodiments, monitoring progression of the in vitro transcription comprises monitoring whether the in vitro transcription is progressing at a desired rate. In certain embodiments, the ability to monitor whether the in vitro transcription is progressing at a desired rate has advantages, including increased yield (e.g., by allowing reaction time to be extended if it is determined that the rate of reaction is slow), improved cost efficiency (e.g., by allowing reaction time to be extended if it is determined that the rate of reaction is slow, such that reactants are not wasted), reduction in the time spent on slow batches, reduced mRNA degradation (e.g., by facilitating identification of conditions that may degrade mRNA and/or minimizing time spent in conditions that may degrade mRNA), and/or easier optimization of reaction conditions (e.g., by facilitating monitoring of the rate of reaction as various conditions are modified), which may increase productivity and/or reduce manufacturing delays.

According to some embodiments, the method comprises determining that the in vitro transcription is progressing at the desired rate. In certain embodiments, the method comprises allowing the in vitro transcription to continue (e.g., until the endpoint is reached) after it has been determined that the in vitro transcription is progressing at the desired rate. In some embodiments where the method comprises allowing the in vitro transcription to continue after it has been determined that the in vitro transcription is progressing at the desired rate, no reaction conditions are modified.

According to some embodiments, the method comprises determining that the in vitro transcription is progressing at a rate lower than the desired rate. In some embodiments, the method comprises stopping the in vitro transcription after it has been determined that the in vitro transcription is progressing at a rate lower than the desired rate. Without wishing to be bound by theory, it is believed that stopping the in vitro transcription after it has been determined that the in vitro transcription is progressing at a rate lower than the desired rate reduces the time spent on slow batches, in some embodiments. In certain embodiments, the method comprises allowing the in vitro transcription to continue (e.g., until the endpoint is reached) after it has been determined that the in vitro transcription is progressing at a rate lower than the desired rate. In certain embodiments where the method comprises allowing the in vitro transcription to continue after it has been determined that the in vitro transcription is progressing at a rate lower than the desired rate, one or more reaction conditions (e.g., temperature, concentration of one or more reactants, concentration of one or more components of an enzyme solution, concentration of one or more components of a buffer solution, and/or rate of mixing) are modified.

According to some embodiments, the method comprises determining that the in vitro transcription is progressing at a rate higher than the desired rate. In some embodiments, the method comprises stopping the in vitro transcription after it has been determined that the in vitro transcription is progressing at a rate higher than the desired rate. In certain embodiments, the method comprises allowing the in vitro transcription to continue (e.g., until the endpoint is reached) after it has been determined that the in vitro transcription is progressing at a rate higher than the desired rate. In certain embodiments where the method comprises allowing the in vitro transcription to continue after it has been determined that the in vitro transcription is progressing at a rate higher than the desired rate, one or more reaction conditions (e.g., temperature, concentration of one or more reactants, concentration of one or more components of an enzyme solution, concentration of one or more components of a buffer solution, and/or rate of mixing) are modified.

As discussed elsewhere herein, in some embodiments, the method comprises stopping the in vitro transcription. In some embodiments, the stopping step occurs after the determining step (e.g., after determining that a reaction condition is not as desired (e.g., the reaction temperature is too low or too high, the mixing rate is too low or too high, the concentration of one or more reactants (e.g., one or more NTPs) is too low or too high, the concentration of one or more components of an enzyme solution is too low or too high, and/or the concentration of one or more components of a buffer solution is too low or too high), determining that the in vitro transcription is not progressing at a desired rate, and/or determining that the in vitro transcription has reached a desired endpoint).

In some embodiments, the stopping step may occur at any suitable time after the determination step. For example, in certain embodiments, the stopping step occurs less than or equal to 5 hours, less than or equal to 4 hours, less than or equal to 3 hours, less than or equal to 2 hours, less than or equal to 1 hour, less than or equal to 45 minutes, less than or equal to 30 minutes, less than or equal to 15 minutes, less than or equal to 10 minutes, less than or equal to 5 minutes, less than or equal to 3 minutes, or less than or equal to 1 minute after the determining step. In some embodiments, the stopping step occurs greater than or equal to 1 second, greater than or equal to 5 seconds, greater than or equal to 15 seconds, greater than or equal to 30 seconds, greater than or equal to 1 minute, greater than or equal to 3 minutes, greater than or equal to 5 minutes, greater than or equal to 10 minutes, greater than or equal to 15 minutes, greater than or equal to 30 minutes, greater than or equal to 45 minutes, greater than or equal to 1 hour, or greater than or equal to 2 hours after the determining step. Combinations of these ranges are also possible (e.g., greater than or equal to 1 second and less than or equal to 5 hours, greater than or equal to 1 second and less than or equal to 5 minutes, or greater than or equal to 15 minutes and less than or equal to 5 hours).

In certain embodiments, the stopping step occurs immediately after the determining step. For example, in certain embodiments, once the determination has been made, the next step will be stopping the in vitro transcription without any steps in between and/or with less than or equal to 5 minutes (e.g., less than or equal to 3 minutes or less than or equal to 1 minute) in between.

In some embodiments, the stopping step occurs before the in vitro transcription would have been stopped absent the determining step. For example, in certain embodiments, the stopping step occurs greater than or equal to 1 second, greater than or equal to 1 minute, greater than or equal to 3 minutes, greater than or equal to 5 minutes, greater than or equal to 10 minutes, greater than or equal to 15 minutes, greater than or equal to 30 minutes, greater than or equal to 45 minutes, greater than or equal to 1 hour, or greater than or equal to 2 hours before the in vitro transcription would have been stopped absent the determining step. In some embodiments, the stopping step occurs less than or equal to 5 hours, less than or equal to 4 hours, less than or equal to 3 hours, less than or equal to 2 hours, less than or equal to 1 hour, less than or equal to 45 minutes, less than or equal to 30 minutes, less than or equal to 15 minutes, less than or equal to 10 minutes, or less than or equal to 5 minutes before the in vitro transcription would have been stopped absent the determining step. Combinations of these ranges are also possible (e.g., greater than or equal to 1 second and less than or equal to 5 hours, greater than or equal to 5 minutes and less than or equal to 1 hour, or greater than or equal to 5 minutes and less than or equal to 3 hours).

According to some embodiments, stopping the in vitro transcription before it would have been stopped absent the determining step has multiple advantages, including increased throughput, reduced mRNA degradation, and/or reduction in the time spent on low-producing and/or slow batches, which may increase productivity and/or reduce manufacturing delays. For example, in certain embodiments where the method comprises determining that the in vitro transcription of a batch is progressing at a rate higher than the desired rate, the in vitro transcription of that batch may be stopped before it would have been absent that determination, allowing another batch to be started early, which increases throughput. As another example, in certain embodiments where the method comprises determining that the reaction temperature is higher than the desired reaction temperature, the mRNA may begin to degrade if left at that temperature for an extended period of time, such that stopping the in vitro transcription before it would have been absent that determination reduces mRNA degradation. In yet another example, in some embodiments where the method comprises determining that the in vitro transcription of a batch is progressing at a rate lower than a desired rate, it may be determined that it would be inefficient to allow that batch to continue, and the in vitro transcription of that batch may be stopped before it would have been absent that determination, allowing another (higher producing) batch to be started early and reducing the time spent on low-producing batches.

In some embodiments, the stopping step occurs after the in vitro transcription would have been stopped absent the determining step. For example, in certain embodiments, the stopping step occurs greater than or equal to 1 second, greater than or equal to 1 minute, greater than or equal to 3 minutes, greater than or equal to 5 minutes, greater than or equal to 10 minutes, greater than or equal to 15 minutes, greater than or equal to 30 minutes, greater than or equal to 45 minutes, greater than or equal to 1 hour, or greater than or equal to 2 hours after the in vitro transcription would have been stopped absent the determining step. In some embodiments, the stopping step occurs less than or equal to 5 hours, less than or equal to 4 hours, less than or equal to 3 hours, less than or equal to 2 hours, less than or equal to 1 hour, less than or equal to 45 minutes, less than or equal to 30 minutes, less than or equal to 15 minutes, less than or equal to 10 minutes, or less than or equal to 5 minutes after the in vitro transcription would have been stopped absent the determining step. Combinations of these ranges are also possible (e.g., greater than or equal to 1 second and less than or equal to 5 hours, greater than or equal to 5 minutes and less than or equal to 1 hour, or greater than or equal to 5 minutes and less than or equal to 3 hours).

According to some embodiments, stopping the in vitro transcription after it would have been stopped absent the determining step has multiple advantages, including increased yield and/or improved cost efficiency, which may increase productivity and/or reduce manufacturing delays. For example, in certain embodiments where the method comprises determining that the in vitro transcription of a batch is progressing at a rate slower than the desired rate, the in vitro transcription of that batch may be stopped after it would have been absent that determination, allowing that batch to have increased yield, which may also improve cost efficiency (e.g., fewer unreacted reactants wasted).

In some embodiments, the method comprises starting a new batch of in vitro transcription. For example, in certain embodiments, the method comprises starting a new batch of in vitro transcription after the stopping step (e.g., using one or more pieces of equipment, such as a bioreactor, that were also used for the batch that was stopped). In certain embodiments, the method comprises starting a new batch of in vitro transcription (e.g., using one or more pieces of equipment, such as a bioreactor, that were also used for the batch that was stopped) less than or equal to 5 hours, less than or equal to 4 hours, less than or equal to 3 hours, less than or equal to 2 hours, less than or equal to 1 hour, less than or equal to 45 minutes, less than or equal to 30 minutes, less than or equal to 15 minutes, less than or equal to 5 minutes, or less than or equal to 3 minutes after the batch was stopped. According to some embodiments, the method comprises starting a new batch of in vitro transcription (e.g., using one or more pieces of equipment, such as a bioreactor, that were also used for the batch that was stopped) greater than or equal to 1 second, greater than or equal to 30 seconds, greater than or equal to 1 minute, greater than or equal to 3 minutes, greater than or equal to 5 minutes, greater than or equal to 10 minutes, greater than or equal to 15 minutes, or greater than or equal to 30 minutes after the batch was stopped. Combinations of these ranges are also possible (e.g., greater than or equal to 1 second and less than or equal to 5 hours, greater than or equal to 1 second and less than or equal to 1 hour, or greater than or equal to 30 seconds and less than or equal to 30 minutes).

In some embodiments, the method comprises optimizing one or more reaction conditions (e.g., temperature, concentration of one or more reactants, concentration of one or more components of an enzyme solution, concentration of one or more components of a buffer solution, and/or rate of mixing) of a subsequent batch of in vitro transcription of mRNA based on data generated from the monitoring step of a previous batch of in vitro transcription. For example, in certain embodiments, the method comprises modifying one or more reaction conditions to increase the rate of reaction, increase yield, increase throughput, and/or reduce mRNA degradation.

In certain embodiments, the methods disclosed herein allow increased consistency in production (e.g., site-to-site, kit-to-kit, and/or batch-to-batch). For example, in embodiments where it is determined that one or more reaction conditions are not as desired and/or the in vitro transcription is not progressing as desired, the method comprises, in certain embodiments, stopping the in vitro transcription (e.g., and starting a new batch instead) and/or modifying one or more reaction conditions, such that batches are consistent.

In some embodiments, the method comprises acquiring one or more Raman spectra during in vitro transcription of mRNA. In certain embodiments, the use of Raman spectroscopy has advantages such as rapid detection (e.g., of reaction conditions and/or progression of the in vitro transcription) and/or real-time monitoring.

In accordance with certain embodiments, the method (e.g., monitoring in vitro transcription of mRNA) comprises using any suitable type and/or number of probes for Raman spectroscopy. For example, in some embodiments, the method comprises using greater than or equal to 1 probe, greater than or equal to 2 probes, greater than or equal to 3 probes, greater than or equal to 4 probes, or greater than or equal to 5 probes. In certain embodiments, the method comprises using less than or equal to 10 probes, less than or equal to 9 probes, less than or equal to 8 probes, less than or equal to 7 probes, less than or equal to 6 probes, less than or equal to 5 probes, less than or equal to 4 probes, less than or equal to 3 probes, or less than or equal to 2 probes. Combinations of these ranges are also possible (e.g., greater than or equal to 1 and less than or equal to 10 probes, greater than or equal to 1 probe and less than or equal to 5 probes, or greater than or equal to 2 probes and less than or equal to 4 probes). In some embodiments, monitoring in vitro transcription of mRNA comprises using one probe for Raman spectroscopy. In certain embodiments, monitoring in vitro transcription of mRNA comprises using two probes for Raman spectroscopy.

In accordance with some embodiments, the method comprises acquiring any suitable number of Raman spectra (e.g., during a batch of in vitro transcription of mRNA). For example, in certain embodiments, the method comprises acquiring greater than or equal to 1, greater than or equal to 3, greater than or equal to 5, greater than or equal to 10, greater than or equal to 25, greater than or equal to 50, greater than or equal to 75, greater than or equal to 100, greater than or equal to 150, greater than or equal to 200, or greater than or equal to 250 Raman spectra during the in vitro transcription of mRNA (e.g., during a batch of in vitro transcription of mRNA). In some embodiments, the method comprises acquiring less than or equal to 500, less than or equal to 400, less than or equal to 300, less than or equal to 250, less than or equal to 200, less than or equal to 150, less than or equal to 100, less than or equal to 75, less than or equal to 50, less than or equal to 25, or less than or equal to 10 Raman spectra during the in vitro transcription of mRNA (e.g., during a batch of in vitro transcription of mRNA). Combinations of these ranges are also possible (e.g., greater than or equal to 1 and less than or equal to 500, greater than or equal to 50 and less than or equal to 400, greater than or equal to 200 and less than or equal to 300, greater than or equal to 1 and less than or equal to 50, greater than or equal to 10 and less than or equal to 150, or greater than or equal to 250 and less than or equal to 500).

According to certain embodiments, the method comprises acquiring Raman spectra using any suitable exposure time for each Raman spectrum. For example, in certain embodiments, the exposure time for each Raman spectrum (e.g., on average) is greater than or equal to 10 milliseconds, greater than or equal to 25 milliseconds, greater than or equal to 50 milliseconds, greater than or equal to 100 milliseconds, greater than or equal to 250 milliseconds, greater than or equal to 500 milliseconds, greater than or equal to 1,000 milliseconds, greater than or equal to 1,500 milliseconds, greater than or equal to 2,000 milliseconds, greater than or equal to 2,500 milliseconds, greater than or equal to 3,000 milliseconds, greater than or equal to 3,500 milliseconds, greater than or equal to 4,000 milliseconds, or greater than or equal to 4,500 milliseconds. In some embodiments, the exposure time for each Raman spectrum (e.g., on average) is less than or equal to 5,000 milliseconds, less than or equal to 4,500 milliseconds, less than or equal to 4,000 milliseconds, less than or equal to 3,500 milliseconds, less than or equal to 3,000 milliseconds, less than or equal to 2,500 milliseconds, less than or equal to 2,000 milliseconds, less than or equal to 1,500 milliseconds, less than or equal to 1,000 milliseconds, less than or equal to 500 milliseconds, less than or equal to 250 milliseconds, or less than or equal to 100 milliseconds. Combinations of these ranges are also possible (e.g., greater than or equal to 10 milliseconds and less than or equal to 5,000 milliseconds, greater than or equal to 100 milliseconds and less than or equal to 4,500 milliseconds, greater than or equal to 1,000 milliseconds and less than or equal to 4,000 milliseconds, greater than or equal to 10 milliseconds and less than or equal to 500 milliseconds, greater than or equal to 100 milliseconds and less than or equal to 2,000 milliseconds, or greater than or equal to 3,000 milliseconds and less than or equal to 5,000 milliseconds).

In accordance with some embodiments, the method comprises acquiring Raman spectra at any suitable interval. For example, in some embodiments, the interval between Raman spectra is greater than or equal to 1 second, greater than or equal to 5 seconds, greater than or equal to 10 seconds, greater than or equal to 15 seconds, greater than or equal to 30 seconds, greater than or equal to 45 seconds, greater than or equal to 1 minute, greater than or equal to 5 minutes, greater than or equal to 10 minutes, greater than or equal to 15 minutes, greater than or equal to 30 minutes, greater than or equal to 45 minutes, or greater than or equal to 1 hour. In certain embodiments, the interval between Raman spectra is less than or equal to 10 hours, less than or equal to 9 hours, less than or equal to 8 hours, less than or equal to 7 hours, less than or equal to 6 hours, less than or equal to 5 hours, less than or equal to 4 hours, less than or equal to 3 hours, less than or equal to 2 hours, less than or equal to 1 hour, less than or equal to 45 minutes, less than or equal to 30 minutes, less than or equal to 15 minutes, less than or equal to 10 minutes, less than or equal to 5 minutes, less than or equal to 2 minutes, or less than or equal to 1 minute. Combinations of these ranges are also possible (e.g., greater than or equal to 1 second and less than or equal to 10 hours, greater than or equal to 15 seconds and less than or equal to 2 hours, greater than or equal to 30 seconds and less than or equal to 30 minutes, greater than or equal to 30 seconds and less than or equal to 2 minutes, greater than or equal to 5 minutes and less than or equal to 30 minutes, greater than or equal to 15 minutes and less than or equal to 1 hour). In some embodiments, the method comprises acquiring Raman spectra continuously.

According to certain embodiments, Raman spectra are acquired at any suitable point in the in vitro transcription. In certain embodiments, the method comprises acquiring Raman spectra throughout the in vitro transcription (e.g., at regular intervals). In some embodiments, the method comprises acquiring Raman spectra during a portion (e.g., at least 10%, at least 25%, at least 50%, at least 75%, or at least 90%) of the in vitro transcription (e.g., at regular intervals).

In accordance with some embodiments, the method comprises starting the acquisition of Raman spectra before the in vitro transcription begins. In accordance with certain embodiments, the method comprises starting the acquisition of Raman spectra when the in vitro transcription begins. According to some embodiments, the method comprises starting the acquisition of Raman spectra after the in vitro transcription begins (e.g., at least 5 minutes, at least 15 minutes, at least 30 minutes, or at least 1 hour after; less than or equal to 2 hours, less than or equal to 1 hour, less than or equal to 30 minutes, or less than or equal to 5 minutes after; combinations of these ranges are also possible, such as after at least 5 minutes and less than or equal to 2 hours after).

In accordance with certain embodiments, the method comprises stopping the acquisition of Raman spectra before the in vitro transcription stops (e.g., at least 5 minutes, at least 15 minutes, at least 30 minutes, or at least 1 hour before; less than or equal to 2 hours, less than or equal to 1 hour, less than or equal to 30 minutes, or less than or equal to 5 minutes before; combinations of these ranges are also possible, such as at least 5 minutes and less than or equal to 2 hours before). In accordance with certain embodiments, the method comprises stopping the acquisition of Raman spectra after the in vitro transcription stops (e.g., at least 5 minutes, at least 15 minutes, at least 30 minutes, or at least 1 hour after; less than or equal to 2 hours, less than or equal to 1 hour, less than or equal to 30 minutes, or less than or equal to 5 minutes after; combinations of these ranges are also possible, such as at least 5 minutes and less than or equal to 2 hours after).

According to some embodiments, the method comprises acquiring Raman spectra using any suitable excitation wavelength. For example, in some embodiments, the method comprises acquiring Raman spectra using an excitation wavelength of greater than or equal to 200 nm, greater than or equal to 300 nm, greater than or equal to 400 nm, greater than or equal to 500 nm, greater than or equal to 600 nm, greater than or equal to 700 nm, greater than or equal to 800 nm, or greater than or equal to 900 nm. In certain embodiments, the method comprises acquiring Raman spectra using an excitation wavelength of less than or equal to 1,000 nm, less than or equal to 900 nm, less than or equal to 800 nm, less than or equal to 700 nm, less than or equal to 600 nm, or less than or equal to 500 nm. Combinations of these ranges are also possible (e.g., greater than or equal to 200 nm and less than or equal to 1,000 nm, greater than or equal to 600 nm and less than or equal to 900 nm, greater than or equal to 700 nm and less than or equal to 800 nm, greater than or equal to 300 nm and less than or equal to 600 nm, or greater than or equal to 800 nm and less than or equal to 1,000 nm).

In accordance with certain embodiments, the method comprises acquiring Raman spectra using any suitable laser power. For example, in certain embodiments, the method comprises acquiring Raman spectra using a laser power of greater than or equal to 25 mW, greater than or equal to 50 mW, greater than or equal to 75 mW, greater than or equal to 100 mW, greater than or equal to 150 mW, greater than or equal to 200 mW, greater than or equal to 250 mW, greater than or equal to 300 mW, greater than or equal to 350 mW, greater than or equal to 400 mW, greater than or equal to 450 mW, greater than or equal to 500 mW, greater than or equal to 600 mW, greater than or equal to 700 mW, greater than or equal to 800 mW, or greater than or equal to 900 mW. In some embodiments, the method comprises acquiring Raman spectra using a laser power of less than or equal to 1,000 mW, less than or equal to 900 mW, less than or equal to 800 mW, less than or equal to 700 mW, less than or equal to 600 mW, less than or equal to 500 mW, less than or equal to 400 mW, less than or equal to 300 mW, less than or equal to 200 mW, or less than or equal to 100 mW, Combinations of these ranges are also possible (e.g., greater than or equal to 25 mW and less than or equal to 1,000 mW, greater than or equal to 300 mW and less than or equal to 700 mW, greater than or equal to 400 mW and less than or equal to 600 mW, greater than or equal to 800 mW and less than or equal to 1,000 mW, or greater than or equal to 100 mW and less than or equal to 300 mW).

In some embodiments, the method comprises averaging multiple Raman spectra (e.g., before comparing the averaged Raman spectra). For example, in certain embodiments, the method comprises averaging greater than or equal to 2, greater than or equal to 3, greater than or equal to 4, greater than or equal to 5, greater than or equal to 10, greater than or equal to 15, greater than or equal to 20, greater than or equal to 25, greater than or equal to 30, greater than or equal to 40, greater than or equal to 50, greater than or equal to 60, greater than or equal to 70, or greater than or equal to 80 Raman spectra. In some embodiments, the method comprises averaging less than or equal to 100, less than or equal to 90, less than or equal to 80, less than or equal to 70, less than or equal to 60, less than or equal to 50, less than or equal to 40, less than or equal to 30, less than or equal to 25, less than or equal to 20, less than or equal to 15, or less than or equal to 10 Raman spectra. Combinations of these ranges are also possible (e.g., greater than or equal to 2 and less than or equal to 100 Raman spectra, greater than or equal to 5 and less than or equal to 25 Raman spectra, greater than or equal to 10 and less than or equal to 40 Raman spectra, greater than or equal to 30 and less than or equal to 50 Raman spectra, or greater than or equal to 50 and less than or equal to 100 Raman spectra). Without wishing to be bound by theory, it is believed that averaging Raman spectra reduces noise.

In certain embodiments, monitoring in vitro transcription of mRNA comprises monitoring the full Raman spectra during one or more Raman spectra. For example, in accordance with certain embodiments, monitoring in vitro transcription of mRNA comprises monitoring the full Raman spectra during one or more Raman spectra to identify any differences. Monitoring the full Raman spectra during one or more Raman spectra to identify any differences includes, in some embodiments, reviewing all peaks to see if any have changed (e.g., appeared, disappeared, or changed in intensity), reviewing multiple peaks to see if certain combinations of peaks have changed (e.g., certain peak changes may be attributed to multiple potential changes such that the specific change can only be identified by reviewing multiple peaks and/or certain reaction condition changes may cause changes in multiple peaks such that the specific condition changes can be better identified by reviewing multiple peaks), reviewing all peaks to see if all have changed, and/or reviewing spectra as a whole (e.g., through the use of an algorithm, such as an algorithm that monitors overall changes in spectra, such as PCA).

For example, in certain embodiments, the full Raman spectra may be different than expected and/or desired due to one or more reaction conditions. For example, if the rate of mixing is too low, the intensity of all (or the majority of) the peaks may drop, in some embodiments, as the various components may separate out (e.g., causing the signals of the majority or all of the components to be masked). As another example, if the concentration or one or more components is too high (e.g., glycerol) that signal may mask the signal of all (or the majority of) the other peaks.

In some embodiments, monitoring in vitro transcription of mRNA comprises monitoring one or more peaks. For example, in certain embodiments, monitoring in vitro transcription of mRNA comprises monitoring changes in one or more peaks (e.g., the appearance of a peak, the disappearance of a peak, the increase in size of a peak, the decrease in size of a peak, and/or a shift in the Raman shift of a peak) in one or more Raman spectra (e.g., over time). In certain embodiments, these peaks are associated with a product (e.g., mRNA), a byproduct (e.g., orthophosphate), one or more components of an enzyme solution (e.g., glycerol), one or more components of a buffer solution (e.g., acetate and/or tris), and/or one or more reactants (e.g., NTPs, such as ATP, GTP, CTP, and/or UTP). For example, in some embodiments, monitoring in vitro transcription of mRNA comprises monitoring changes in one or more peaks associated with a product (e.g., mRNA), a byproduct (e.g., orthophosphate), and/or one or more reactants (e.g., NTPs, such as ATP, GTP, CTP, and/or UTP).

In some embodiments, monitoring in vitro transcription of mRNA comprises monitoring one or more peaks at greater than or equal to 200 cm$^{-1}$, greater than or equal to 250 cm$^{-1}$, greater than or equal to 300 cm$^{-1}$, greater than or equal to 350 cm$^{-1}$, greater than or equal to 400 cm$^{-1}$, greater than or equal to 450 cm$^{-1}$, greater than or equal to 500 cm$^{-1}$, greater than or equal to 550 cm$^{-1}$, greater than or equal to 600 cm$^{-1}$, greater than or equal to 650 cm$^{-1}$, greater than or equal to 700 cm$^{-1}$, greater than or equal to 750 cm$^{-1}$, greater than or equal to 800 cm$^{-1}$, greater than or equal to 825 cm$^{-1}$, greater than or equal to 850 cm$^{-1}$, greater than or equal to 875 cm$^{-1}$, greater than or equal to 900 cm$^{-1}$, greater than or equal to 920 cm$^{-1}$, greater than or equal to 950 cm$^{-1}$, greater than or equal to 970 cm$^{-1}$, greater than or equal to 1,000 cm$^{-1}$, greater than or equal to 1,025 cm$^{-1}$, greater than or equal to 1,040 cm$^{-1}$, greater than or equal to 1,050 cm$^{-1}$, greater than or equal to 1,075 cm$^{-1}$, greater than or equal to 1,100 cm$^{-1}$, greater than or equal to 1,125 cm$^{-1}$, greater than or equal to 1,150 cm$^{-1}$, greater than or equal to 1,175 cm$^{-1}$, greater than or equal to 1,200 cm$^{-1}$, greater than or equal to 1,250 cm$^{-1}$, greater than or equal to 1,300 cm$^{-1}$, greater than or equal to 1,350 cm$^{-1}$, greater than or equal to 1,400 cm$^{-1}$, greater than or equal to 1,450 cm$^{-1}$, greater than or equal to 1,500 cm$^{-1}$, greater than or equal to 1,550 cm$^{-1}$, greater than or equal to 1,600 cm$^{-1}$, greater than or equal to 1,700 cm$^{-1}$, greater than or equal to 1,800 cm$^{-1}$, greater than or equal to 1,900 cm$^{-1}$, greater than or equal to 2,000 cm$^{-1}$, greater than or equal to 2,250 cm$^{-1}$, greater than or equal to 2,500 cm$^{-1}$, greater than or equal to 2,750 cm$^{-1}$, or greater than or equal to 3,000 cm$^{-1}$ of one or more Raman spectra. In certain embodiments, monitoring in vitro transcription of mRNA comprises monitoring one or more peaks at less than or equal to 3,300 cm$^{-1}$, less than or equal to 3,000 cm$^{-1}$, less than or equal to 2,750 cm$^{-1}$, less than or equal to 2,500 cm$^{-1}$, less than or equal to 2,250 cm$^{-1}$, less than or equal to 2,000 cm$^{-1}$, less than or equal to 1,900 cm$^{-1}$, less than or equal to 1,800 cm$^{-1}$, less than or equal to 1,700 cm$^{-1}$, less than or equal to 1,650 cm$^{-1}$, less than or equal to 1,600 cm$^{-1}$, less than or equal to 1,550 cm$^{-1}$, less than or equal to 1,500 cm$^{-1}$, less than or equal to 1,450 cm$^{-1}$, less than or equal to 1,400 cm$^{-1}$, less than or equal to 1,350 cm$^{-1}$, less than or equal to 1.300 cm$^{-1}$, less than or equal to 1,250 cm$^{-1}$, less than or equal to 1,200 cm$^{-1}$, less than or equal to 1,175 cm$^{-1}$, less than or equal to 1,150 cm 1, less than or equal to 1,120 cm$^{-1}$, less than or equal to 1,100 cm$^{-1}$, less than or equal to 1,070 cm$^{-1}$, less than or equal to 1,050 cm$^{-1}$, less than or equal to 1,025 cm$^{-1}$, less than or equal to 1,000 cm$^{-1}$, less than or equal to 975 cm$^{-1}$, less than or equal to 940 cm$^{-1}$, less than or equal to 900 cm$^{-1}$, less than or equal to 880 cm$^{-1}$, less than or equal to 850 cm$^{-1}$, less than or equal to 800 cm$^{-1}$, less than or equal to 700 cm$^{-1}$, less than or equal to 600 cm$^{-1}$, or less than or equal to 500 cm$^{-1}$ of one or more Raman spectra. Combinations of these ranges are also possible (e.g., greater than or equal to 200 cm$^{-1}$ and less than or equal to 3,300 cm$^{-1}$, greater than or equal to 970 cm$^{-1}$ and less than or equal to 1,000 cm$^{-1}$, greater than or equal to 1,100 cm$^{-1}$ and less than or equal to 1,120 cm$^{-1}$, greater than or equal to 1,150 cm$^{-1}$ and less than or equal to 1,650 cm$^{-1}$, greater than or equal to 800 cm$^{-1}$ and less than or equal to 880 cm$^{-1}$, greater than or equal to 920 cm$^{-1}$ and less than or equal to 940 cm$^{-1}$, or greater than or equal to 1,040 cm$^{-1}$ and less than or equal to 1,070 cm$^{-1}$).

In certain embodiments, monitoring in vitro transcription of mRNA comprises monitoring the formation of mRNA. In some embodiments, monitoring comprises monitoring one or more peaks (e.g., monitoring the appearance of a peak and/or the increase in size of a peak) at about 790-840 cm$^{-1}$ (e.g., 800-830 cm$^{-1}$) and/or about 1070-1130 cm$^{-1}$ (e.g., 1090-1110 cm$^{-1}$). For example, in some embodiments, monitoring comprises monitoring the formation of mRNA by monitoring one or more peaks (e.g., monitoring intensity of one or more peaks) at about 790-840 cm$^{-1}$ (e.g., 800-830 cm$^{-1}$) and/or about 1070-1130 cm$^{-1}$ (e.g., 1090-1110 cm$^{-1}$). In some embodiments, monitoring in vitro transcription of mRNA comprises monitoring the formation of one or more byproducts (e.g., orthophosphate) (e.g., of one or more Raman spectra) (e.g., over time). For example, in certain embodiments, monitoring in vitro transcription of mRNA comprises monitoring the formation of orthophosphate (HPO$_4^{2-}$). During in vitro transcription, in some embodiments, each NTP addition results in formation of inorganic pyrophosphate (PPi), which is hydrolyzed by pyrophosphatase (PPase) to orthophosphate, as shown in the following equations:

$$(RNA)_n + \text{Mg}NTP(RNA)_{n+1} \rightarrow \text{MgP}_2\text{O}_7^{2-} + \text{H}^+$$

$$\text{MgP}_2\text{O}_7^{2-} + \text{H}_2\text{O} \rightleftharpoons 2\text{HPO}_4^{2-} + \text{Mg}^{2+}$$

Accordingly, in some embodiments, the rate of production of mRNA, the amount of mRNA produced, and/or the stage of the in vitro transcription (e.g., relative to the endpoint) may be determined from the rate of formation of orthophosphate and/or the amount of orthophosphate produced.

In certain embodiments, monitoring comprises monitoring one or more peaks (e.g., monitoring the appearance of a peak and/or the increase in size of a peak) at about 970-1000 cm$^{-1}$. For example, in some embodiments, monitoring comprises monitoring the formation of orthophosphate by monitoring a peak (e.g., monitoring intensity of a peak) at about 970-1000 cm$^{-1}$.

According to some embodiments, monitoring comprises monitoring the reduction in concentration of one or more reactants, such as one or more NTPs (e.g., ATP, GTP, CTP, and/or UTP, and/or total NTPs) (e.g., over time) (e.g., of one or more Raman spectra). During in vitro transcription, each NTP addition results in a reduction in concentration of an NTP, such that the rate of production of mRNA, the amount of mRNA produced, and/or the stage of the in vitro transcription (e.g., relative to the endpoint) may be determined based on the rate of reduction of one or more NTPs (e.g., total NTPs) and/or the amount of one or more NTPs (e.g., total NTPS), in certain embodiments. In some embodiments, the concentration of one or more NTPs is monitored by monitoring a peak at about 700-800 cm$^{-1}$ and/or 1100-1700 cm$^{-1}$ (e.g., 1150-1650 cm$^{-1}$). For example, according to some embodiments, the concentration of GTP is monitored by monitoring a peak at about 1560-1600 cm$^{-1}$ (e.g., 1570-1590 cm$^{-1}$) and/or a peak at about 1470-1500 cm$^{-1}$ (e.g., 1480-1495 cm$^{-1}$). According to certain embodiments, the concentration of ATP is monitored by monitoring a peak at about 710-750 cm$^{-1}$ (e.g., 720-740 cm$^{-1}$). According to some embodiments, the concentration of CTP is monitored by monitoring a peak at about 770-800 cm$^{-1}$ (e.g., 775-790 cm$^{-1}$). According to some embodiments, the concentration of UTP is monitored by monitoring a peak at about 780-810 cm$^{-1}$ (e.g., 785-805 cm$^{-1}$), 1220-1240 cm$^{-1}$, and/or 1660-1680 cm$^{-1}$. In certain embodiments, the concentration of total NTPs is monitored by monitoring a peak at about 1100-1120 cm$^{-1}$. In some embodiments, the concentration of an individual NTP is monitored and/or determined by monitoring and/or determining the concentration of total NTPs and the concentration of the other individual NTPs present. For example, if GTP, ATP, CTP, and UTP were present, the concentration of UTP may be monitored and/or determined by monitoring and/or determining the total NTP concentration and the concentrations of GTP, ATP, and CTP, and subtracting those concentrations from the total NTP concentration.

In certain embodiments, monitoring comprises monitoring one or more peaks (e.g., monitoring the disappearance of a peak and/or the decrease in size of a peak) at about 1100-1120 cm$^{-1}$ and/or one at about 1150-1650 cm$^{-1}$. For example, in some embodiments, monitoring comprises monitoring the reduction in concentration of one or more NTPs by monitoring one or more peaks at about 1100-1120 cm$^{-1}$. As another example, in certain embodiments, monitoring comprises monitoring the reduction in concentration of total NTPs by monitoring one or more peaks at about 1150-1650 cm$^{-1}$.

In accordance with certain embodiments, monitoring comprises monitoring concentration of one or more components of one or more enzyme solutions (e.g., of one or more Raman spectra) (e.g., over time). In some embodiments, the concentration of one or more components of one or more enzyme solutions is monitored by monitoring one or more peaks at about 800-880 cm$^{-1}$. For example, in certain embodiments, the concentration of glycerol in one or more enzyme solutions is monitored by monitoring one or more peaks at about 800-880 cm$^{-1}$.

According to some embodiments, monitoring comprises monitoring concentration of one or more components of one or more buffers (e.g., of one or more Raman spectra) (e.g., over time). In accordance with certain embodiments, the concentration of one or more components of a buffer is monitoring by monitoring one or more peaks at about 920-940 cm$^{-1}$ and/or one or more peaks at about 1040-1070 cm$^{-1}$. For example, in some embodiments, the concentration of acetate in one or more buffers is monitored by monitoring one or more peaks at about 920-940 cm$^{-1}$. In certain embodiments, the concentration of tris in one or more buffers is monitored by monitoring one or more peaks at about 1040-1070 cm$^{-1}$.

In some embodiments, the method (e.g., the monitoring and/or the determining) comprises using an algorithm (e.g., to analyze the Raman spectra) (e.g., to determine whether the in vitro transcription has reached a desired endpoint, whether the in vitro transcription is progressing at a desired rate, and/or whether one or more reaction conditions are as desired). In certain embodiments, the algorithm comprises Principal Component Analysis (PCA) and/or a Batch Evolution Model. According to certain embodiments, PCA transforms the data for each variable (e.g., the data for each wavenumber) into data for a new set of variables called Principal Components (PCs). In certain embodiments, PC1 is a combination of wavenumbers with the largest change over time, while PC2 is a combination of wavenumbers with the second largest change over time, and so on. According to some embodiments, plotting PC1 over time generates a single curve representative of the overall changes in the spectra over time. In accordance with some embodiments, the single curve generated by PCA (e.g., for one batch) (e.g., PC1) may be compared to another single curve generated by PCA (e.g., for another batch and/or a desired PCA curve) (e.g., PC1) rather than comparing the spectra directly.

According to some embodiments, the method (e.g., the monitoring and/or the determining) comprises comparing one or more Raman spectra and/or representations thereof (e.g., spectra analyzed by an algorithm, such as PCA and/or a Batch Evolution Model) to one or more reference Raman spectra and/or representations thereof (e.g., from a prior batch) to identify the presence of one or more differences. In certain embodiments, the presence of one or more differences may be identified through visual comparison and/or statistical analysis. In some embodiments, the method further comprises identifying the cause of the one or more differences that are present (e.g., differences in one or more reaction conditions).

In accordance with certain embodiments, in vitro mRNA transcription comprises a batch process, a fed-batch process, and/or a continuous process. It should be understood that the term "batch" is used herein for convenience, but description using the term "batch" should not be interpreted to be limited to in vitro mRNA transcription comprising a batch process, as such description may also apply to other process types, such as fed-batch processes and/or continuous processes, in some embodiments.

As used herein, mRNA is a type of RNA, which is a type of "nucleic acid." It should be understood that any disclosure herein that refers to "RNA" or "nucleic acid" may also apply to mRNA.

As used herein, the term "nucleic acid" refers to multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G))). As used herein, the term nucleic acid refers to polyribonucleotides as well as polydeoxyribonucleotides. The term nucleic acid shall also include polynucleosides (i.e., a polynucleotide minus the phosphate) and any other organic base containing polymer. Non-limiting examples of nucleic acids include chromosomes, genomic loci, genes or gene segments that encode polynucleotides or polypeptides, coding sequences, non-coding sequences (e.g., intron, 5'-UTR, or 3'-UTR) of a gene, pri-mRNA, pre-mRNA, cDNA, mRNA, etc. A nucleic acid (e.g., mRNA) may include a substitution and/or modification. In some embodiments, the substitution and/or modification is in one or more bases and/or sugars. For example, in some embodiments a nucleic acid (e.g., mRNA) includes nucleic acids having backbone sugars that are covalently attached to low molecular weight organic groups other than a hydroxyl group at the 2' position and other than a phosphate group or hydroxy group at the 5' position. Thus, in some embodiments, a substituted or modified nucleic acid (e.g., mRNA) includes a 2'-O-alkylated ribose group. In some embodiments, a modified nucleic acid (e.g., mRNA) includes sugars such as hexose, 2'-F hexose, 2'-amino ribose, constrained ethyl (cEt), locked nucleic acid (LNA), arabinose or 2'-fluoroarabinose instead of ribose. Thus, in some embodiments, a nucleic acid (e.g., mRNA) is heterogeneous in backbone composition thereby containing any possible combination of polymer units linked together such as peptide-nucleic acids (which have an amino acid backbone with nucleic acid bases).

In some embodiments, a nucleic acid is DNA, RNA, PNA, cEt, LNA, ENA or hybrids including any chemical or natural modification thereof. Chemical and natural modifications are well known in the art. Non-limiting examples of modifications include modifications designed to increase translation of the nucleic acid, to increase cell penetration or sub-cellular distribution of the nucleic acid, to stabilize the nucleic acid against nucleases and other enzymes that degrade or interfere with the structure or activity of the nucleic acid, and to improve the pharmacokinetic properties of the nucleic acid.

In some embodiments, the RNA has an open reading frame (ORF) encoding a polypeptide. In some embodiments, the RNA is a messenger RNA (mRNA). In some embodiments, the RNA (e.g., mRNA) further comprises a 5' UTR, 3' UTR, a poly(A) tail and/or a 5' cap analog.

Messenger RNA (mRNA) is any RNA that encodes a (at least one) protein (a naturally-occurring, non-naturally-occurring, or modified polymer of amino acids) and can be translated to produce the encoded protein in vitro, in vivo, in situ, or ex vivo. The skilled artisan will appreciate that, except where otherwise noted, nucleic acid sequences set forth in the instant application may recite "T"s in a representative DNA sequence but where the sequence represents RNA (e.g., mRNA), the "T"s would be substituted for "U"s. Thus, any of the DNAs disclosed and identified by a particular sequence identification number herein also disclose the corresponding RNA (e.g., mRNA) sequence complementary to the DNA, where each "T" of the DNA sequence is substituted with "U."

An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences disclosed herein may further comprise additional elements, e.g., 5' and 3' UTRs, but that those elements, unlike the ORF, need not necessarily be present in an RNA polynucleotide of the present disclosure.

Naturally-occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, an RNA polynucleotide (e.g., mRNA) has an open reading frame encoding at least one polypeptide having at least one modification and at least one 5' terminal cap. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, MA). 5'-capping of modified RNA may be completed post-transcriptionally using a Vaccinia Virus Capping Enzyme to generate the "Cap 0" structure: m7G(5')ppp(5')G (New England Bio-Labs, Ipswich, MA). Cap 1 structure may be generated using both Vaccinia Virus Capping Enzyme and a 2'-O methyltransferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes may be derived from a recombinant source. A cap analog may be, for example, a dinucleotide cap, a trinucleotide cap, or a tetranucleotide cap. In some embodiments, a cap analog is a dinucleotide cap. In some embodiments, a cap analog is a trinucleotide cap. In some embodiments, a cap analog is a tetranucleotide cap. As used here the term "cap" includes the inverted G nucleotide and can comprise additional nucleotides 3' of the inverted G, e.g., 1, 2, or more nucleotides 3' of the inverted G and 5' to the 5' UTR.

The 3'-poly(A) tail is typically a stretch of adenine nucleotides added to the 3'-end of the transcribed mRNA. A polyA tail may contain 10 to 400 adenosine monophosphates. For example, a poly A tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300, 350, or 400 adenosine monophosphates. It can, in some instances, comprise up to about 400 adenine nucleotides. In some embodiments, the length of the 3'-poly(A) tail may be an essential element with respect to the stability of the individual mRNA.

In some embodiments, an RNA (e.g., mRNA) has an ORF that encodes a signal peptide fused to the expressed polypeptide. Signal peptides, comprising the N-terminal 15-60 amino acids of proteins, can aid in the translocation across the membrane on the secretory pathway and, thus, can control the entry of proteins both in eukaryotes and prokaryotes to the secretory pathway.

In some embodiments, an ORF encoding a polypeptide is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, an RNA (e.g., mRNA) is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g., A, G, C, or U). In some embodiments, nucleotides and nucleosides of the present disclosure comprise standard deoxyribonucleosides such as those present in DNA (e.g., dA, dG, dC, or dT).

In some embodiments, an RNA (e.g., mRNA) has an open reading frame encoding a polypeptide, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

In some embodiments, modified nucleobases in nucleic acids (e.g., RNA nucleic acids, such as mRNA nucleic acids) comprise 1-methyl-pseudouridine (m1), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a mRNA of the disclosure comprises 1-methyl-pseudouridine (m1ψ) substitutions at one or more or all uridine positions of the nucleic acid.

In some embodiments, a mRNA of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a mRNA of the disclosure comprises pseudouridine (ψ) substitutions at one or more or all uridine positions of the nucleic acid.

In some embodiments, a mRNA of the disclosure comprises pseudouridine (ψ) substitutions at one or more or all uridine positions of the nucleic acid and 5-methyl cytidine substitutions at one or more or all cytidine positions of the nucleic acid.

In some embodiments, a mRNA of the disclosure comprises uridine at one or more or all uridine positions of the nucleic acid.

In some embodiments, mRNAs are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G. U. C) may be uniformly modified in a nucleic acid of the disclosure, or in a predetermined sequence region thereof (e.g., in the mRNA including or excluding the poly(A) tail). In some embodiments, all nucleotides X in a nucleic acid of the present disclosure (or in a sequence region thereof) are modified nucleotides, wherein X may be any one of nucleotides A, G. U. C, or any one of the combinations A+G, A+U, A+C, G+U, G+C, U+C, A+G+U, A+G+C, G+U+C or A+G+C.

The mRNAs of the present disclosure may comprise one or more regions or parts which act or function as an untranslated region. Where mRNAs are designed to encode at least one polypeptide of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas, the 3' UTR starts immediately following the stop codon and continues until the transcriptional termination signal. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

In some embodiments, the nucleic acid (e.g., RNA, such as mRNA) comprises greater than or equal to 400 nucleotides, greater than or equal to 500 nucleotides, greater than or equal to 600 nucleotides, greater than or equal to 800 nucleotides, greater than or equal to 1,000 nucleotides, greater than or equal to 1,500 nucleotides, greater than or equal to 2,000 nucleotides, greater than or equal to 3,000 nucleotides, greater than or equal to 4,000 nucleotides, greater than or equal to 5,000 nucleotides, greater than or equal to 6,000 nucleotides, greater than or equal to 7,000 nucleotides, or greater than or equal to 8,000 nucleotides. In certain embodiments, the nucleic acid (e.g., RNA, such as mRNA) comprises less than or equal to 15,000 nucleotides, less than or equal to 14,000 nucleotides, less than or equal to 13,000 nucleotides, less than or equal to 12,000 nucleotides, less than or equal to 11,000 nucleotides, 10,000 nucleotides, less than or equal to 9,000 nucleotides, less than or equal to 8,000 nucleotides, less than or equal to 7,000 nucleotides, or less than or equal to 6,000 nucleotides. Combinations of these ranges are also possible (e.g., greater than or equal to 400 nucleotides and less than or equal to 15,000 nucleotides or greater than or equal to 4,000 nucleotides and less than or equal to 6,000 nucleotides).

In certain embodiments, the nucleic acid (e.g., RNA, such as mRNA) encodes a therapeutic protein. In some embodiments the nucleic acid is an mRNA designed to achieve particular biologic effects (e.g., as a vaccine). Exemplary vaccines of the invention feature mRNAs encoding a particular antigen of interest (or an mRNA or mRNAs encoding antigens of interest). In exemplary aspects, the mRNA encodes antigen(s) derived from diseases, such as infectious diseases or cancers.

Diseases or conditions, in some embodiments, include those caused by or associated with infectious agents, such as bacteria, viruses, fungi and parasites. Non-limiting examples of such infectious agents include Gram-negative bacteria, Gram-positive bacteria, RNA viruses (including (+)ssRNA viruses, (−)ssRNA viruses, dsRNA viruses), DNA viruses (including dsDNA viruses and ssDNA viruses), reverse transcriptase viruses (including ssRNA-RT viruses and dsDNA-RT viruses), protozoa, helminths, and ectoparasites.

In some embodiments, the antigen comprises an infectious disease antigen. The antigen of the infectious disease vaccine is a viral or bacterial antigen, in some embodiments.

The vaccines may be traditional or personalized cancer or infectious disease vaccines.

In some embodiments, "administering" or "administration" means providing a material to a subject in a manner that is pharmacologically useful. In some embodiments, a composition or nucleic acid (e.g., mRNA) disclosed herein is administered to a subject enterally. In some embodiments, an enteral administration of the composition or nucleic acid (e.g., mRNA) is oral. In some embodiments, a composition or nucleic acid (e.g., mRNA) disclosed herein is administered to the subject parenterally. In some embodiments, a composition or nucleic acid (e.g., mRNA) disclosed herein is administered to a subject subcutaneously, intraocularly, intravitreally, subretinally, intravenously (IV), intracerebroventricularly, intramuscularly, intrathecally (IT), intracisternally, intraperitoneally, via inhalation, topically, or by direct injection to one or more cells, tissues, or organs.

To "treat" a disease as the term is used herein, means to reduce the frequency or severity of at least one sign or symptom of a disease, disorder or condition experienced by a subject. The compositions or nucleic acids (e.g., mRNAs) described above or elsewhere herein are typically administered to a subject in an effective amount, that is, an amount capable of producing a desirable result. The desirable result will depend upon the active agent being administered. For example, an effective amount of a nucleic acid (e.g., mRNA) or a composition comprising a nucleic acid (e.g., mRNA) may be an amount that is capable of increasing expression of a protein in the subject. A therapeutically acceptable amount may be an amount that is capable of treating a disease or condition, e.g., a disease or condition that that can be relieved by increasing expression of a protein in a subject. As is well known in the medical and veterinary arts, dosage for any one subject depends on many factors, including the subject's size, body surface area, age, the particular composition to be administered, the active ingredient(s) in the composition (e.g., mRNA), the intended outcome of the administration, time and route of administration, general health, and other drugs being administered concurrently.

Some embodiments comprise administering to a subject an mRNA produced during an IVT reaction monitored by Raman spectroscopy.

In some embodiments, method A comprises acquiring one or more Raman spectra during in vitro transcription of mRNA. In certain embodiments of method A, the method comprises performing in vitro transcription of mRNA. In certain embodiments of method A, the method comprises monitoring one or more reaction conditions and/or progression of the in vitro transcription. In some embodiments of method A, the method comprises determining whether the in vitro transcription has reached a desired endpoint, whether the in vitro transcription is progressing at a desired rate, and/or whether one or more reaction conditions are as desired. In certain embodiments of method A, the method further comprises modifying one or more reaction conditions after the determining step. In some embodiments of method A, the one or more reaction conditions comprises temperature, concentration of one or more reactants, concentration of one or more components of one or more enzyme solutions, concentration of one or more components of one or more buffer solutions, and/or rate of mixing. In certain embodiments of method A, the modifying one or more reaction conditions increases reaction rate, increases yield, and/or reduces mRNA degradation. According to some embodiments of method A, the method further comprises determining whether the in vitro transcription has reached a desired endpoint and/or whether the in vitro transcription is progressing at a desired rate.

In accordance with certain embodiments of method A, the method further comprises determining that the in vitro transcription is occurring at a temperature below a desired temperature. According to certain embodiments of method A, the method further comprises increasing the temperature of the in vitro transcription. In accordance with some embodiments of method A, the method further comprises increasing the temperature of the in vitro transcription from the temperature below the desired temperature to the desired temperature.

In certain embodiments of method A, the method further comprises determining that the in vitro transcription is occurring at a temperature above a desired temperature. In some embodiments of method A, the method further comprises decreasing the temperature of the in vitro transcription. According to certain embodiments of method A, the method further comprises decreasing the temperature of the in vitro transcription from the temperature above the desired temperature to the desired temperature.

According to some embodiments of method A, the method further comprises determining that one or more reactants are present at a concentration higher than a desired concentration or at a concentration lower than the desired concentration of the one or more reactants. In accordance with certain embodiments of method A, the one or more reactants comprises a nucleoside triphosphate. In accordance with some embodiments of method A, the one or more reactants comprises adenosine triphosphate, guanosine triphosphate, cytidine triphosphate, and/or uridine triphosphate. In certain embodiments of method A, the method further comprises increasing the concentration of the one or more reactants present at a concentration lower than the desired concentration of the one or more reactants.

In some embodiments of method A, the method further comprises determining that one or more components of one or more enzyme solutions is present at a concentration lower than a desired concentration of the one or more components of one or more enzyme solutions. According to certain embodiments of method A, the method further comprises increasing the concentration of the one or more components of one or more enzyme solutions. According to some embodiments of method A, the method further comprises increasing the concentration of the one or more components of one or more enzyme solutions to the desired concentration of the one or more components of one or more enzyme solutions. In accordance with certain embodiments of method A, the enzyme comprises an RNA polymerase. In accordance with some embodiments of method A, the RNA polymerase comprises a T7 polymerase enzyme.

In certain embodiments of method A, the method further comprises determining that the in vitro transcription has reached a desired endpoint. In some embodiments of method A, the method further comprises determining that the in vitro transcription has not yet reached a desired endpoint. According to certain embodiments of method A, the method further comprises determining that the in vitro transcription is progressing at a rate lower than a desired rate or at a rate higher than the desired rate.

According to some embodiments of method A, the method further comprises determining that the in vitro transcription is occurring with a rate of mixing below a desired rate of mixing or a rate of mixing above the desired rate of mixing. In accordance with certain embodiments of method A, the method further comprises increasing and/or decreasing the rate of mixing. In accordance with some embodiments of method A, the method further comprises increasing the rate of mixing below the desired rate of mixing to the desired rate of mixing. In certain embodiments of method A, the method further comprises decreasing the rate of mixing above the desired rate of mixing to the desired rate of mixing.

In some embodiments of method A, the method further comprises determining that one or more components of one or more buffer solutions is present at a concentration lower than a desired concentration of the one or more components of one or more buffer solutions. According to certain embodiments of method A, the method further comprises increasing the concentration of the one or more components of one or more buffer solutions. According to some embodiments of method A, the method further comprises increasing the concentration of the one or more components of one or more buffer solutions to the desired concentration of the one or more components of one or more buffer solutions.

In certain embodiments of method A, the method further comprises monitoring whether all of the desired components of the in vitro transcription are present in a batch. In some embodiments of method A, the method further comprises determining that one or more of the desired components of the in vitro transcription are not present in the batch. According to certain embodiments of method A, the method further comprises adding the component that is not present to the batch, making the determination not to begin in vitro transcription with the batch, and/or making the determination to start a new in vitro transcription batch.

In accordance with certain embodiments of method A, the method further comprises stopping the in vitro transcription after the determining step. In accordance with some embodiments of method A, the stopping step occurs immediately after the determining step. In certain embodiments of method A, the stopping step occurs before the in vitro transcription would have been stopped absent the determining step. In some embodiments of method A, the stopping step occurs after the in vitro transcription would have been stopped absent the determining step. According to certain embodiments of method A, the stopping step occurs greater than or equal to 1 second and less than or equal to 5 hours after the determining step. According to some embodiments of method A, the stopping step occurs greater than or equal to 1 second and less than or equal to 5 minutes after the determining step. In accordance with certain embodiments of method A, the method further comprises starting a new batch of in vitro transcription after the stopping step.

According to certain embodiments of method A, the method further comprises performing and/or monitoring one or more post-in vitro transcription processes. In some embodiments of method A, the post-in vitro transcription processes comprises Tangential Flow Filtration (TFF). According to some embodiments of method A, the method further comprises monitoring the presence and/or concentration of one or more components of in vitro transcription during the post-in vitro transcription process. In certain embodiments of method A, the method further comprises first determining that one or more components of in vitro transcription are still present and/or are at a higher concentration than desired, and then continuing the post-in vitro transcription process.

In accordance with some embodiments of method A, the method further comprises optimizing one or more reaction conditions of a subsequent batch of in vitro transcription based on data generated from the monitoring step.

In certain embodiments of method A, the mRNA comprises greater than or equal to 400, 500, 1,000, 2,000, 3,000, 4,000, 5,000, 6,000, 7,000, or 8,000 nucleotides. In some embodiments of method A, the mRNA comprises greater than or equal to 400 nucleotides. According to certain embodiments of method A, the mRNA comprises greater than or equal to 4,000 nucleotides. According to some embodiments of method A, the mRNA comprises less than or equal to 15,000, 14,000, 13,000, 12,000, 11,000, 10,000, 9,000, 8,000, 7,000, or 6,000 nucleotides. In accordance with certain embodiments of method A, the mRNA comprises less than or equal to 10,000 nucleotides. In accordance with some embodiments of method A, the mRNA comprises less than or equal to 6,000 nucleotides.

In certain embodiments of method A, the mRNA encodes a therapeutic protein. In some embodiments of method A, the mRNA encodes an antigen. According to certain embodiments of method A, the antigen is an infectious disease antigen. According to some embodiments of method A, the infectious disease is caused by or associated with a virus. In accordance with certain embodiments of method A, the antigen is a cancer antigen. In accordance with some embodiments of method A, the cancer antigen is a personalized cancer antigen.

According to some embodiments of method A, the monitoring comprises monitoring a peak representative of mRNA. In certain embodiments of method A, the monitoring comprises monitoring formation of one or more byproducts. In some embodiments of method A, the monitoring comprises monitoring formation of orthophosphate. According to certain embodiments of method A, the monitoring comprises monitoring reduction in concentration of one or more reactants. According to some embodiments of method A, the monitoring comprises monitoring reduction in concentration of one or more nucleoside triphosphates (NTPs). In accordance with certain embodiments of method A, the monitoring comprises monitoring reduction in concentration of total nucleoside triphosphates (NTPs).

In accordance with some embodiments of method A, the monitoring comprises monitoring one or more full Raman spectra. In certain embodiments of method A, the monitoring comprises monitoring one or more peaks of one or more Raman spectra. In some embodiments of method A, the monitoring comprises monitoring one or more peaks at greater than or equal to 970 cm$^{-1}$ and less than or equal to 1000 cm$^{-1}$ of one or more Raman spectra. According to certain embodiments of method A, the monitoring comprises monitoring one or more peaks at greater than or equal to 1100 cm$^{-1}$ and less than or equal to 1120 cm$^{-1}$ of one or more Raman spectra. According to some embodiments of method A, the monitoring comprises monitoring one or more peaks at greater than or equal to 1150 cm$^{-1}$ and less than or equal to 1650 cm$^{-1}$ of one or more Raman spectra. In accordance with certain embodiments of method A, the monitoring comprises monitoring one or more peaks at greater than or equal to 800 cm$^{-1}$ and less than or equal to 880 cm$^{-1}$ of one or more Raman spectra. In accordance with some embodiments of method A, the monitoring comprises monitoring one or more peaks at greater than or equal to 920 cm-' and less than or equal to 940 cm$^{-1}$ of one or more Raman spectra. In certain embodiments of method A, the monitoring comprises monitoring one or more peaks at greater than or equal to 1040 cm$^{-1}$ and less than or equal to 1070 cm$^{-1}$ of one or more Raman spectra.

In some embodiments of method A, the acquiring one or more Raman spectra comprises acquiring greater than or equal to 1 and less than or equal to 500 Raman spectra during a batch of in vitro transcription of mRNA. According to certain embodiments of method A, the acquiring one or more Raman spectra comprises acquiring Raman spectra using an exposure time of greater than or equal to 10 milliseconds and less than or equal to 5,000 milliseconds.

According to some embodiments of method A, the acquiring one or more Raman spectra comprises acquiring Raman spectra at an interval of greater than or equal to 1 second and less than or equal to 10 hours. In accordance with certain embodiments of method A, the acquiring one or more Raman spectra comprises acquiring Raman spectra throughout the in vitro transcription. In accordance with some embodiments of method A, the acquiring one or more Raman spectra comprises acquiring Raman spectra using an excitation wavelength of greater than or equal to 200 nm and less than or equal to 1,000 nm. In certain embodiments of method A, the acquiring one or more Raman spectra comprises acquiring Raman spectra using a laser power of greater than or equal to 25 mW and less than or equal to 1,000 mW. In accordance with some embodiments of method A, the method comprises using greater than or equal to 1 probe for Raman spectroscopy and less than or equal to 10 probes for Raman spectroscopy. In some embodiments of method A, the method comprises averaging greater than or equal to 2 and less than or equal to 100 Raman spectra.

According to certain embodiments of method A, the monitoring comprises using an algorithm (e.g., to determine whether the in vitro transcription has reached a desired endpoint, whether the in vitro transcription is progressing at a desired rate, and/or whether one or more reaction conditions are as desired). According to some embodiments of method A, the algorithm comprises Principal Component Analysis (PCA). In accordance with certain embodiments of method A, the algorithm comprises a Batch Evolution Model.

In accordance with some embodiments of method A, the monitoring comprises comparing one or more Raman spectra and/or representations thereof to one or more reference Raman spectra and/or representations thereof to identify the presence of one or more differences. In certain embodiments of method A, the method further comprises identifying the cause of the one or more differences that are present.

In some embodiments of method A, the in vitro mRNA transcription comprises a batch process. According to certain embodiments of method A, the in vitro mRNA transcription comprises a fed-batch process. According to some embodiments of method A, the in vitro mRNA transcription comprises a continuous process.

The following examples are intended to illustrate certain embodiments of the present invention, but do not exemplify the full scope of the invention. Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

EXAMPLES

Example 1

This example describes the monitoring of in vitro transcription of mRNA using Raman spectroscopy.

A 100 mL batch of in vitro transcription of mRNA was run at 37° C. using a T7 polymerase enzyme. The reaction was monitored over time using Raman spectroscopy. An overlay of all of the spectra obtained with grayscale to show time (with black being the first spectrum and white being the last spectrum) is presented in FIG. 1A. Each spectrum (in FIGS. 1A, 3A, 4A, and 5A) is an average of multiple spectra surrounding a given timepoint to reduce noise. From FIG. 1A, it was determined which peaks were expected to change over time and how they were expected to change, and which peaks were expected to stay the same over time.

Figure 1B:
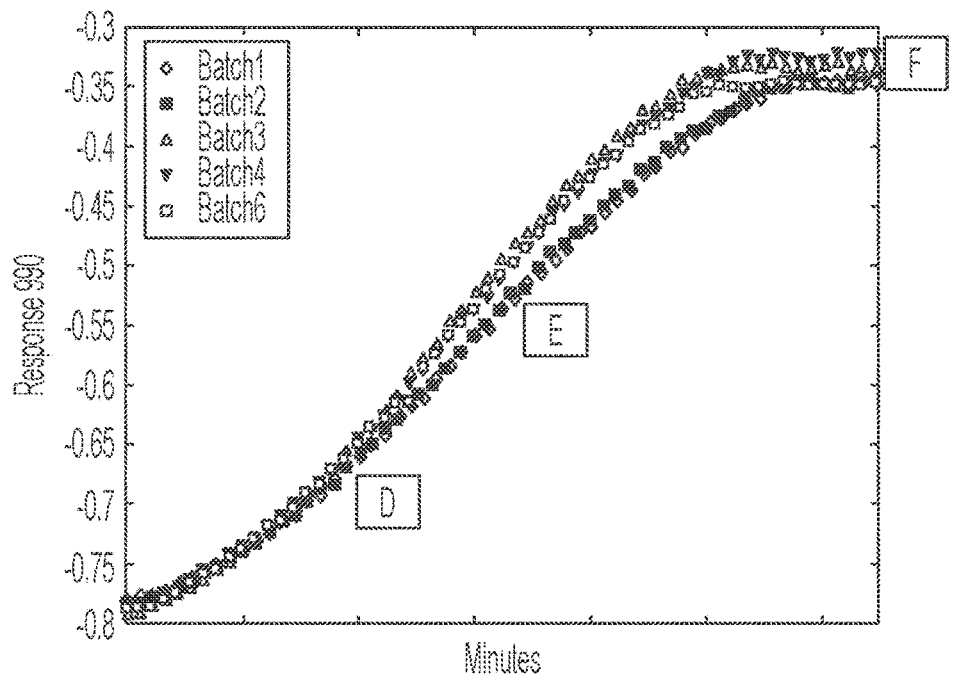
FIG. 1B shows the normalized intensity (y-axis labeled Response 990) of the orthophosphate peak(s) (box B from FIG. 1A) versus time (in minutes) for the five batches from FIG. 1A. Box D represents a first timepoint, box E represents a second timepoint, and box F represents the endpoint.

To monitor the rate of in vitro transcription of mRNA, the normalized intensity (y-axis, labeled Response 990) of an orthophosphate peak (representative of total mRNA) was plotted versus time (in minutes), as shown in FIG. 1B. It was determined that the rate of reaction for in vitro mRNA transcription may be determined using Raman spectroscopy. For example, the rate of reaction may be determined from FIG. 1B using the following equation:

$$\text{Rate of Reaction}(R) = (I_2 - I_1)/(T_2 - T_1)$$

as discussed in more detail elsewhere herein. For example, in FIG. 1B, the first timepoint for determining the rate of reaction may be that represented by box D and the second timepoint for determining the rate of reaction may be that represented by box E, as the portion of the curve between box D and box E is linear.

It was further determined that the endpoint could be identified using Raman spectroscopy. For example, as shown in FIG. 1B, the endpoint of the in vitro mRNA transcription was identified as the time when the normalized intensity of the orthophosphate peak (representative of total mRNA) leveled off and no longer continued to increase at a significant rate (see, e.g., the timepoint represented by box F in FIG. 1B).

Similarly, it was further determined that the endpoint could be predicted using Raman spectroscopy. For example, in some embodiments, once the rate of reaction and the intensity of the endpoint (e.g., of the orthophosphate peak, which is representative of total mRNA) are determined as described above, the timing of the endpoint may be determined for future batches with the same yield using the following equation:

$$T_{end} = (I_{end})/R$$

where $T_{end}$ is the time at the endpoint, $I_{end}$ is the normalized intensity of the orthophosphate peak (representative of total mRNA) peaks at the endpoint, and R is the rate of reaction determined as described above.

Figure 1C:
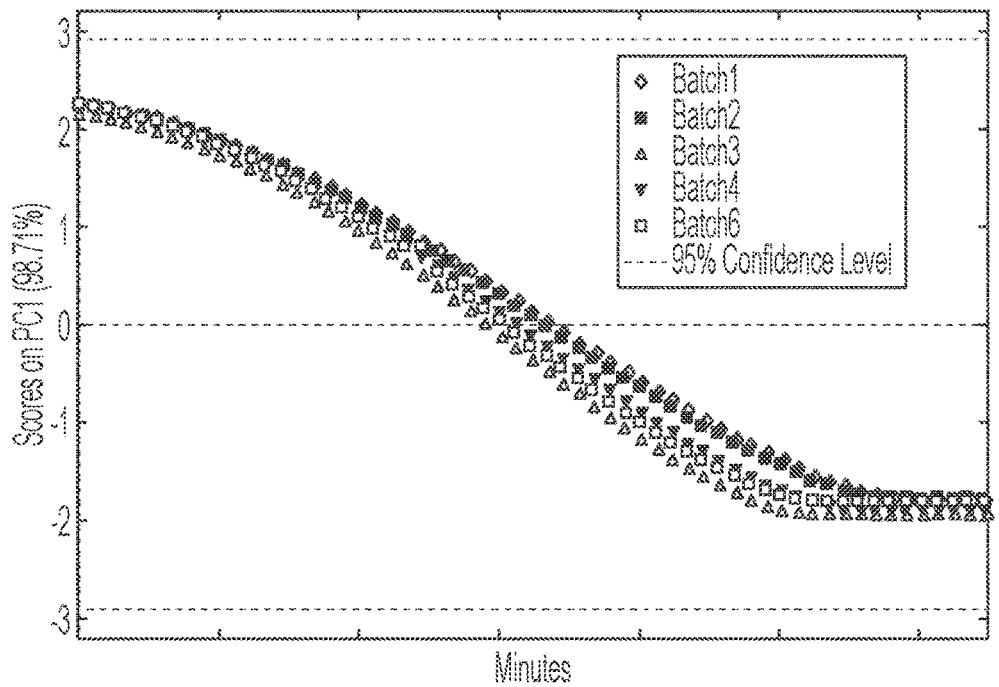
FIG. 1C plots the Scores on PC1 versus time (in minutes) for the five batches from FIGS. 1A-1B based on full spectral information using PCA.

Moreover, it was determined that, in some embodiments, these determinations (e.g., rate of reaction, endpoint intensity, and/or endpoint time) can be made using PCA (see FIG. 1C) using the full spectrum or using any portions of the spectrum (e.g., portions of the spectrum representative of the concentration of one or more reactants, the concentration of one or more products, and/or the concentration of one or more byproducts) that are directly correlated with the in vitro transcription of mRNA (e.g., they increase or decrease at the same rate relative to the rate of in vitro transcription). When using other portions of the spectrum, the equations above may be modified such that I (e.g., $I_2$, $I_1$, and $I_{end}$) represents the value on the y-axis at that time, and T (e.g., $T_2$, $T_1$, and $T_{end}$) represents the value on the x-axis. When using other portions of the spectrum, the endpoint may still be identified as the point where the y-axis values level off and no longer change significantly.

For example, it was determined that monitoring a Raman peak associated with orthophosphate ($[HPO_4]^{2-}$) (e.g., at 990 cm$^{-1}$) may be used to monitor in vitro mRNA transcription, in certain embodiments, rather than directly monitoring peaks associated with the mRNA itself. During in vitro transcription, in some embodiments, each NTP addition results in formation of inorganic pyrophosphate (PPi), which is hydrolyzed by pyrophosphatase (PPase) to orthophosphate, as shown in the following equations:

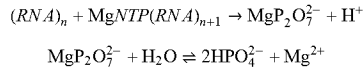

$$(RNA)_n + MgNTP(RNA)_{n+1} \rightarrow MgP_2O_7^{2-} + H^+$$

$$MgP_2O_7^{2-} + H_2O \rightleftharpoons 2HPO_4^{2-} + Mg^{2+}$$

Accordingly, determination of the rate of formation (or amount) of orthophosphate allows determination of the rate of formation (or amount) of the mRNA, as 2 moles of orthophosphate are formed for every mole of NTP consumed, in some embodiments.

Figure 1D:
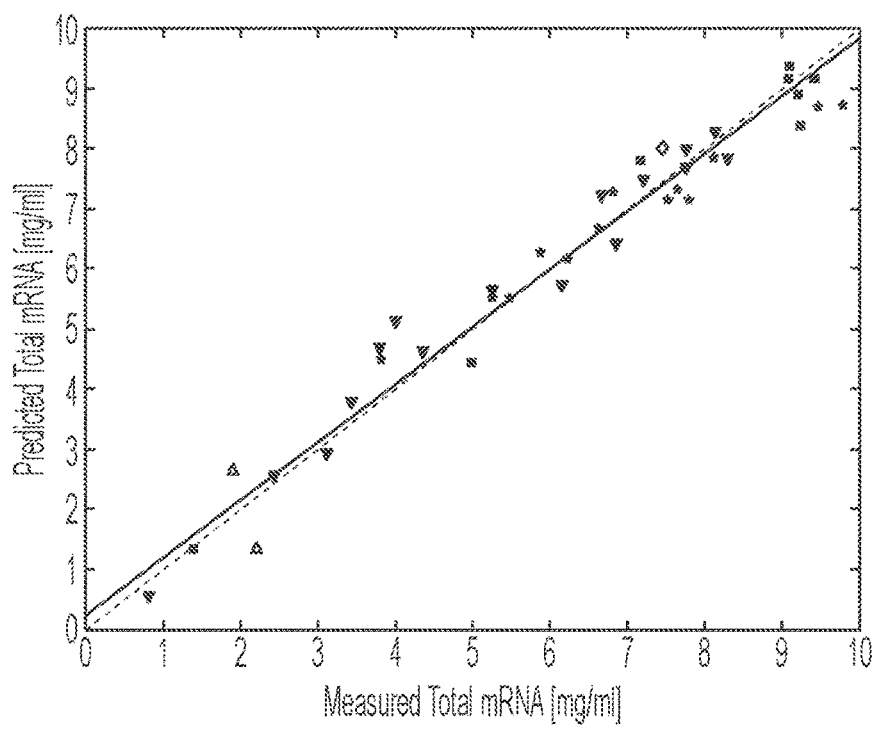
FIG. 1D plots total mRNA (mg/mL) predicted by monitoring peak(s) associated with orthophosphate versus total mRNA (mg/mL) measured with HPLC.

The calculated concentration of total mRNA based on observing the portion of the Raman spectrum associated with orthophosphate at a given time point was plotted versus the concentration of total mRNA at the same timepoint as measured using HPLC (see FIG. 1D). As shown in FIG. 1D, determining the concentration of total mRNA by observing the portion of the Raman spectrum associated with orthophosphate worked well as plotting the calculated versus measured values had an $R^2$ value of approximately 0.96.

Figure 1E:
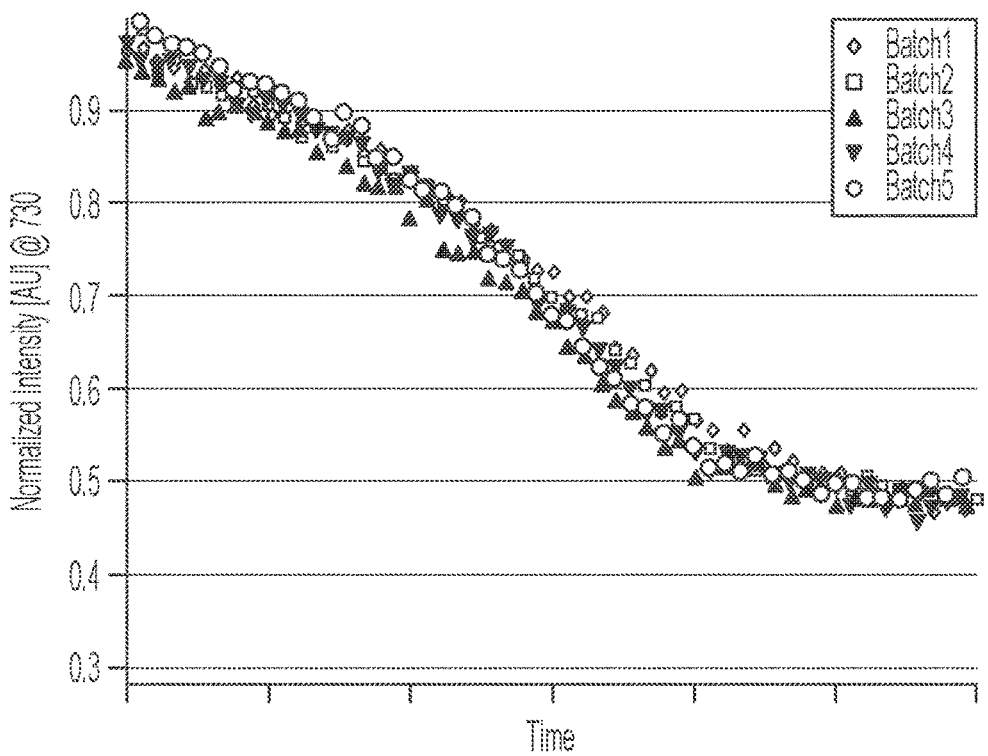
FIG. 1E plots normalized intensity of a Raman peak at 730 $cm^{-1}$—representative of ATP
versus time for five batches of in vitro mRNA transcription.
Figure 1F:
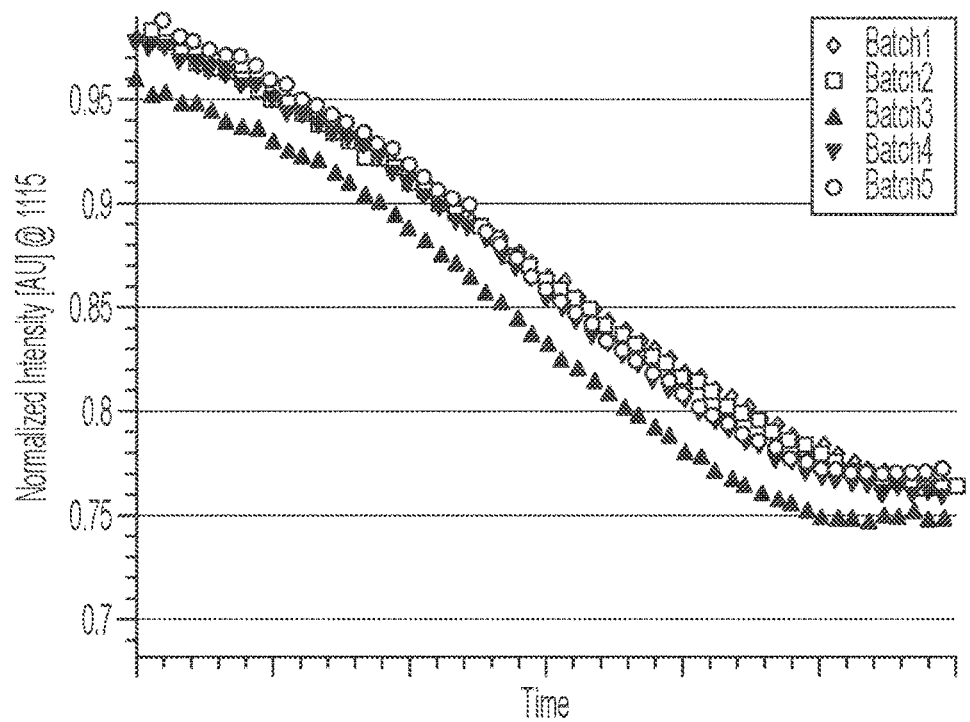
FIG. 1F plots normalized intensity of a Raman peak at 1115 $cm^{-1}$—representative of total NTPs—versus time for five batches of in vitro mRNA transcription.
Figure 1G:
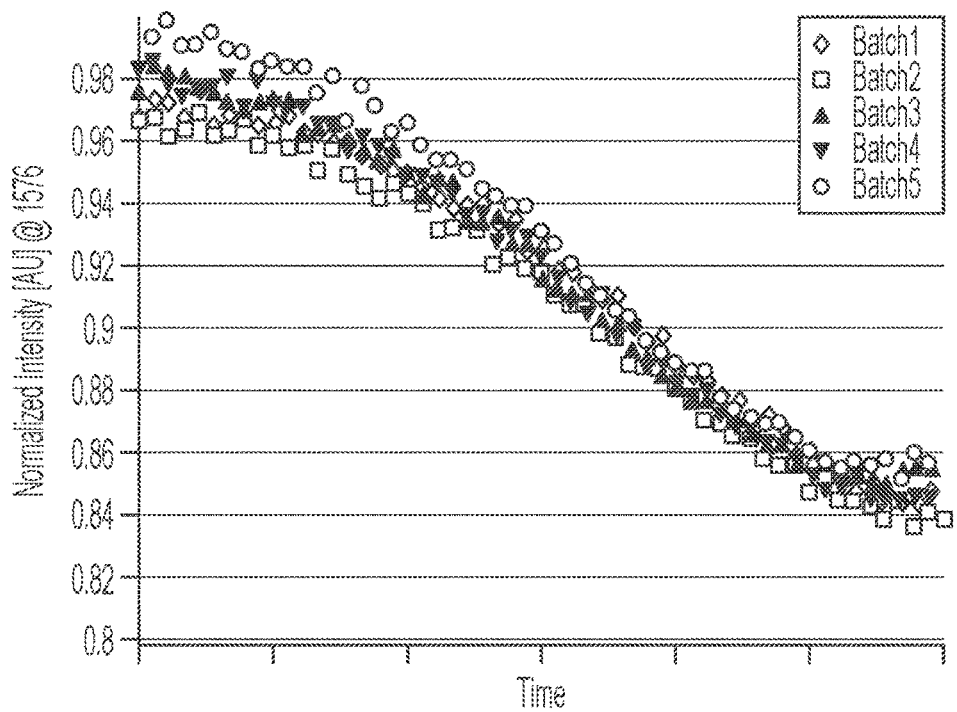
FIG. 1G plots normalized intensity of a Raman peak at 1576 $cm^{-1}$—representative of GTP—versus time for five batches of in vitro mRNA transcription.

It was also determined that monitoring a Raman peak associated with reactants (e.g., total NTPs, or individual NTPs, such as ATP or GTP) may be used to monitor in vitro mRNA transcription, in certain embodiments, as the concentration of reactants will decrease as in vitro mRNA transcription progresses. For example, FIG. 1E shows how ATP levels decreased as in vitro mRNA transcription progressed for five batches, FIG. 1F shows how total NTP levels decreased as in vitro mRNA transcription progressed for five batches, and FIG. 1G shows how GTP levels decreased as in vitro mRNA transcription progressed for five batches.

These findings indicate that Raman spectroscopy may be a valuable tool for monitoring in vitro transcription of mRNA, including determination of the rate of reaction and endpoint, in certain instances.

Example 2

This example describes the monitoring of three batches of in vitro mRNA transcription wherein the conditions differed only in reaction temperature: a normal temperature batch (37) ° C., a low temperature batch (35° C.), and a high temperature batch (39° C.).

Figure 2:
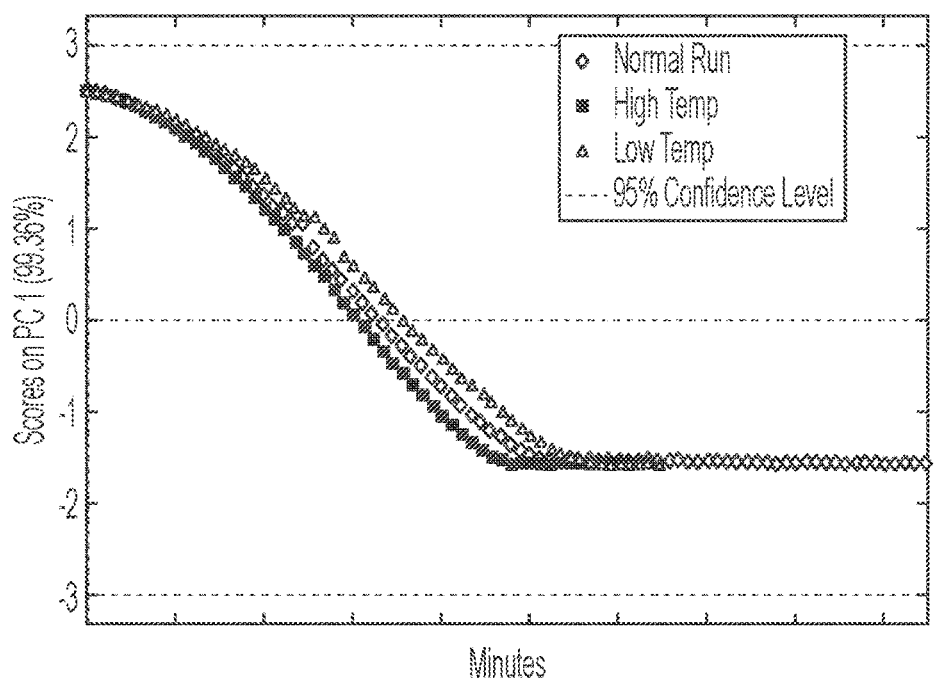
FIG. 2 plots the Scores on PC1 versus time (in minutes) based on full spectral information using PCA for three batches of in vitro mRNA transcription over time wherein the conditions differ only in reaction temperature: a normal temperature batch (37° C.), a low temperature batch (35° C.), and a high temperature batch (39° C.).

The spectra obtained for each of the three batches over time (where each spectrum was an average of multiple spectra surrounding a given timepoint to reduce noise) were substantially identical. However, as shown in FIG. 2, when the Scores on PC1 were plotted versus time (in minutes) for the three batches, there was a difference in the rate of reaction and time of the endpoint for the three batches, with the high temperature batch reaching the endpoint first, followed by the normal temperature batch, and then followed by the low temperature batch.

This example demonstrates that the temperature affects the rate of reaction and endpoint time, in some cases, and that Raman spectroscopy may be used to determine whether the temperature is at the desired temperature (or above or below).

Example 3

This example describes the monitoring of two batches of in vitro mRNA transcription wherein the conditions differed only in the concentration of nucleoside triphosphates (NTPs): the high NTP concentration batch had a 20% higher concentration of each NTP than the normal batch.

Figure 3A:
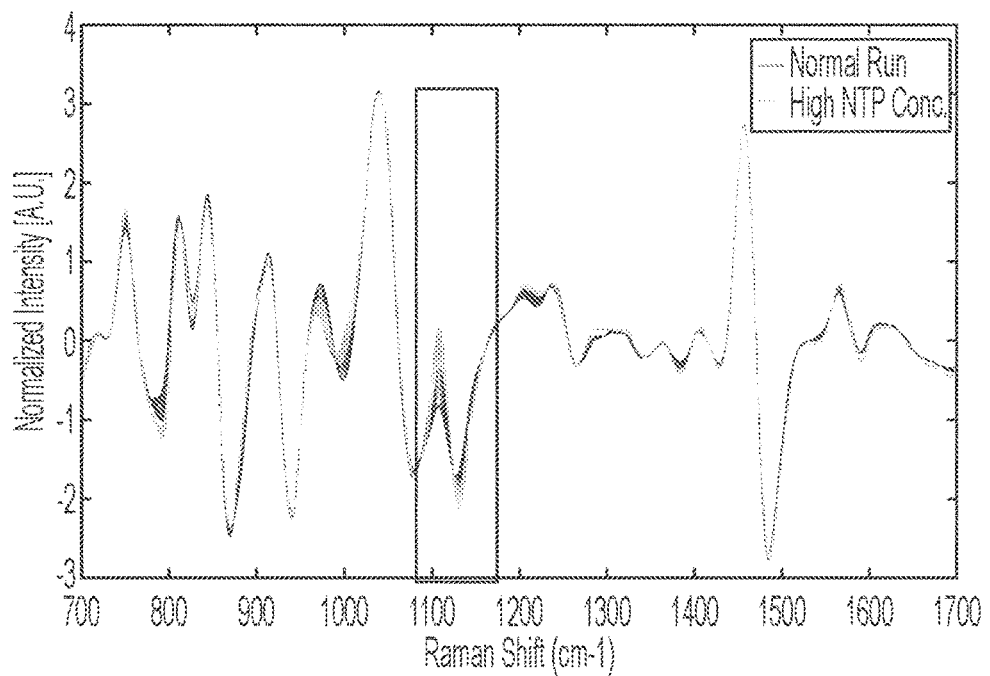
FIG. 3A shows an overlay of Raman spectra (plotting normalized intensity (AU) versus Raman shift ($cm^{-1}$)) for two batches of in vitro mRNA transcription over time wherein the conditions differ only in the concentration of nucleoside triphosphates (NTPs): the high NTP concentration batch has a 20% higher concentration of each NTP than the normal batch. The box shows a portion of the spectra with substantial differences.
Figure 3B:
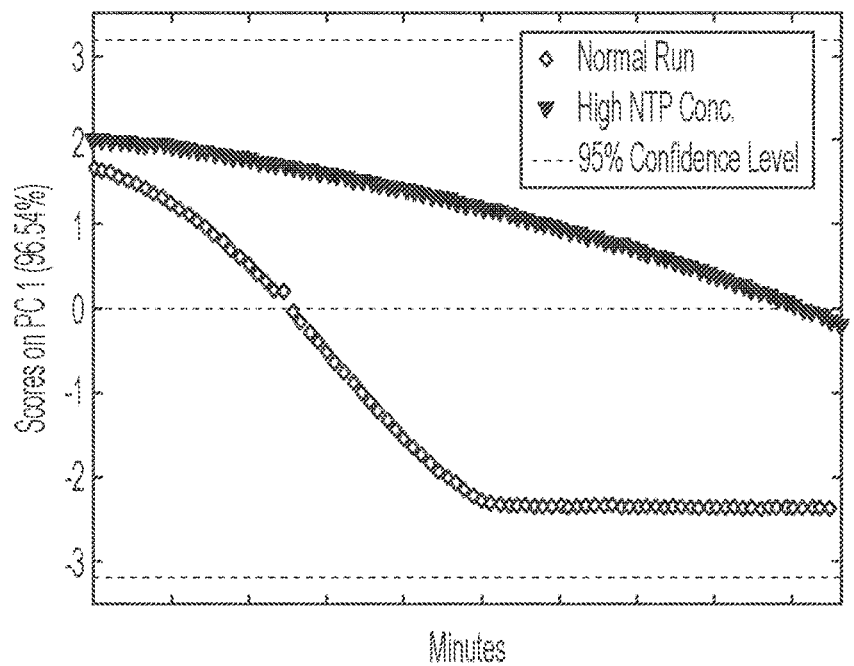
FIG. 3B plots the Scores on PC1 versus time (in minutes) for the two batches from FIG. 3A based on full spectral information using PCA.

An overlay of all of the spectra obtained for each of the two batches over time is presented in FIG. 3A. As shown in FIG. 3A, certain peaks in the Raman spectrum (e.g., the peaks in the box in FIG. 3A) of the high NTP concentration batch had higher intensities than the same peaks in the normal batch. Moreover, as shown in FIG. 3B, when the Scores on PC1 were plotted versus time (in minutes) for the two batches, there was a substantial difference in the rate of reaction and time of the endpoint for the two batches, with the high NTP concentration batch having a slower rate of reaction and reaching the endpoint much later, if ever. Without wishing to be bound by theory, it is believed that the high NTP concentration inhibited the in vitro transcription.

This example demonstrates that the concentration of NTPs affects the rate of reaction and endpoint time, and that Raman spectroscopy may be used to determine whether the NTP concentration is at the desired concentration (or above or below), in certain embodiments.

Example 4

This example describes the monitoring of two batches of in vitro mRNA transcription wherein the conditions differed only in the concentration of the T7 polymerase enzyme: the low T7 concentration batch had a 20% lower T7 polymerase enzyme concentration than the normal batch.

Figure 4A:
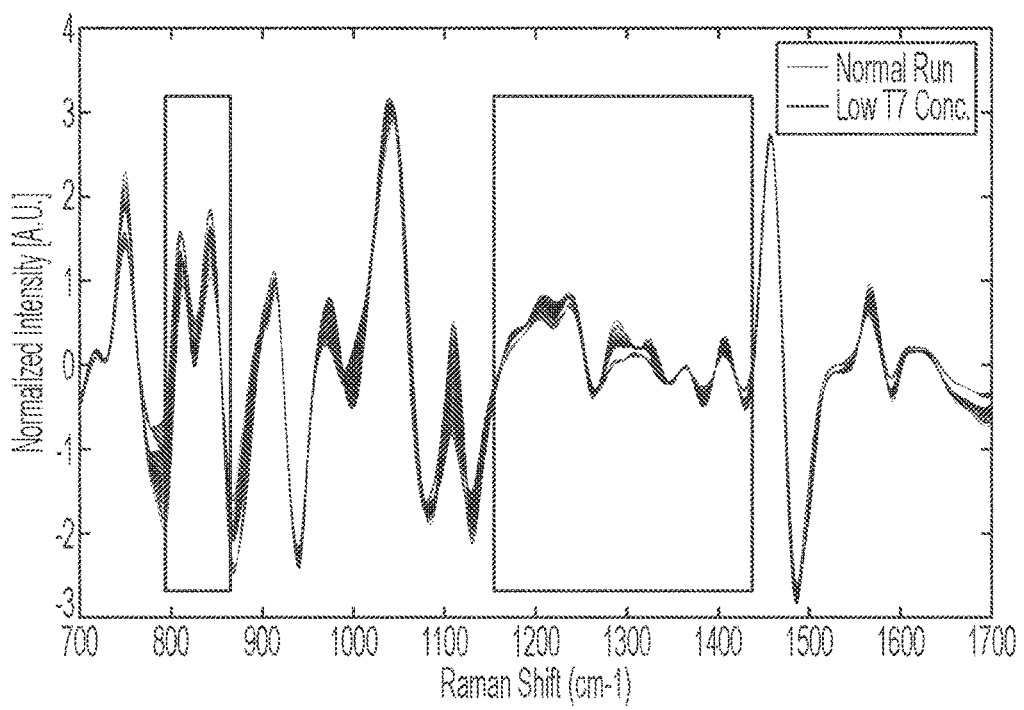
FIG. 4A shows an overlay of Raman spectra (plotting normalized intensity (AU) versus Raman shift ($cm^{-1}$)) for two batches of in vitro mRNA transcription over time wherein the conditions differ only in the concentration of the T7 polymerase enzyme solution: the low T7 concentration batch has a 20% lower concentration of the T7 polymerase enzyme solution than the normal batch. The boxes show portions of the spectra with substantial differences.
Figure 4B:
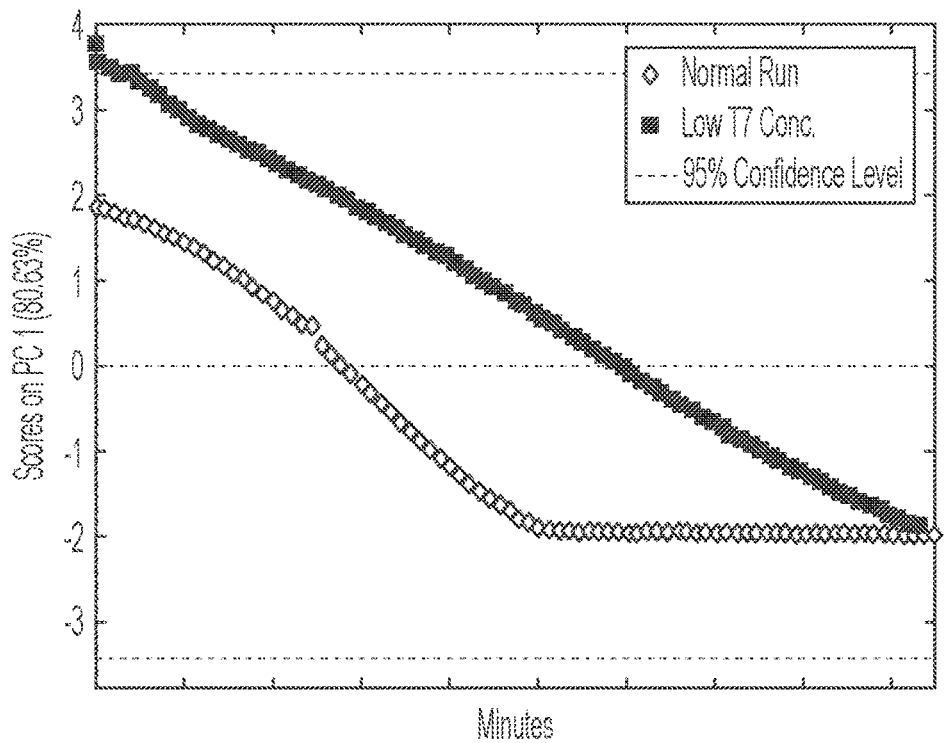
FIG. 4B plots the Scores on PC1 versus time (in minutes) for the two batches from FIG. 4A based on full spectral information using PCA.

An overlay of all of the spectra obtained for each of the two batches over time is presented in FIG. 4A. As shown in FIG. 4A, certain peaks in the Raman spectrum (e.g., the peaks in the boxes in FIG. 4A, which are representative of the concentration of glycerol in the enzyme solution) of the low T7 concentration batch had different intensities than the same peaks in the normal batch. Moreover, as shown in FIG. 4B, when the Scores on PC1 were plotted versus time (in minutes) for the two batches, there was a substantial difference in the rate of reaction and time of the endpoint for the two batches, with the low T7 concentration batch having a slower rate of reaction and reaching the endpoint much later.

This example demonstrates that the concentration of the T7 polymerase enzyme affects the rate of reaction and endpoint time, and that Raman spectroscopy may be used to determine whether the T7 polymerase enzyme concentration is at the desired concentration (or above or below), in some instances.

Example 5

This example describes the monitoring of two batches of in vitro mRNA transcription wherein the conditions differed only in the ratios between the concentrations of NTPs: the NTP Ratios batch swapped concentrations of ATP and UTP and swapped the concentrations of GTP and CTP compared to the normal batch (i.e., the concentration of ATP in the normal batch was instead the concentration of UTP in the NTP Ratios batch, the concentration of UTP in the normal batch was instead the concentration of ATP in the NTP Ratios batch, the concentration of GTP in the normal batch was instead the concentration of CTP in the NTP Ratios batch, and the concentration of CTP in the normal batch was instead the concentration of GTP in the NTP Ratios batch).

Figure 5A:
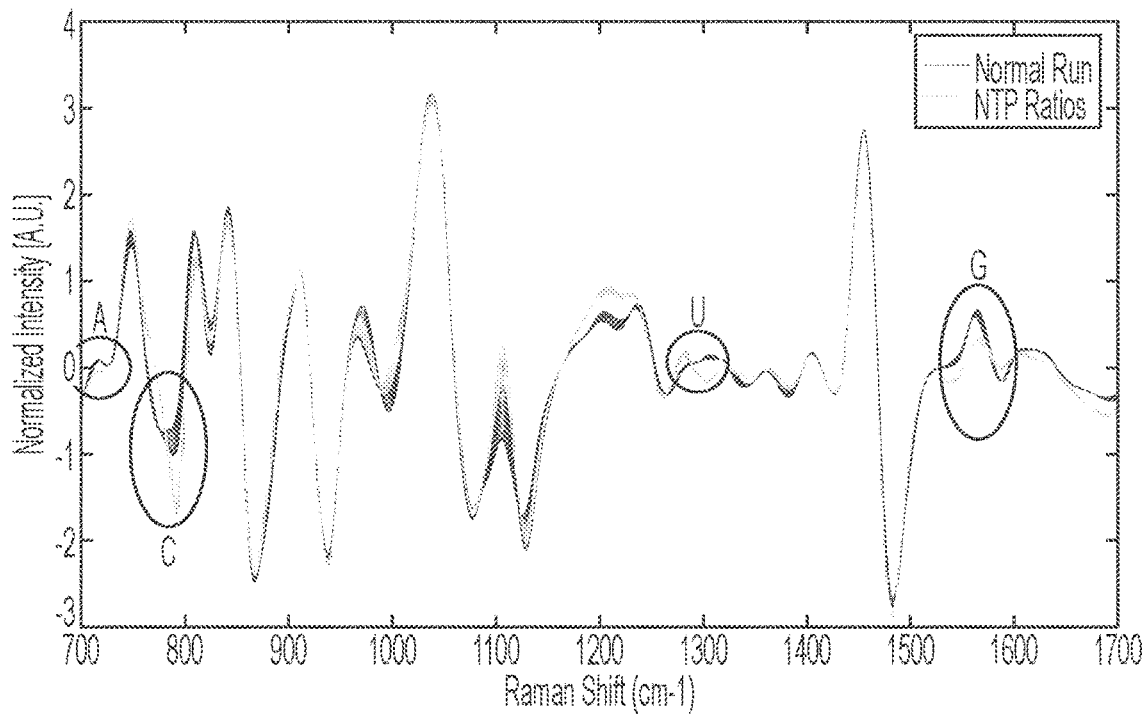
FIG. 5A shows an overlay of Raman spectra (plotting normalized intensity (AU) versus Raman shift ($cm^{-1}$)) for two batches of in vitro mRNA transcription over time wherein the conditions differ only in the ratios between the concentrations of NTPs: the NTP Ratios batch swapped the concentrations of ATP and UTP and swapped the concentrations of GTP and CTP compared to the normal batch. The circles show portions of the spectra with substantial differences: circle A is associated with the difference in concentration of ATP, circle C is associated with the difference in concentration of CTP, circle U is associated with the difference in concentration of UTP, and circle G is associated with the difference in concentration of GTP.
Figure 5B:
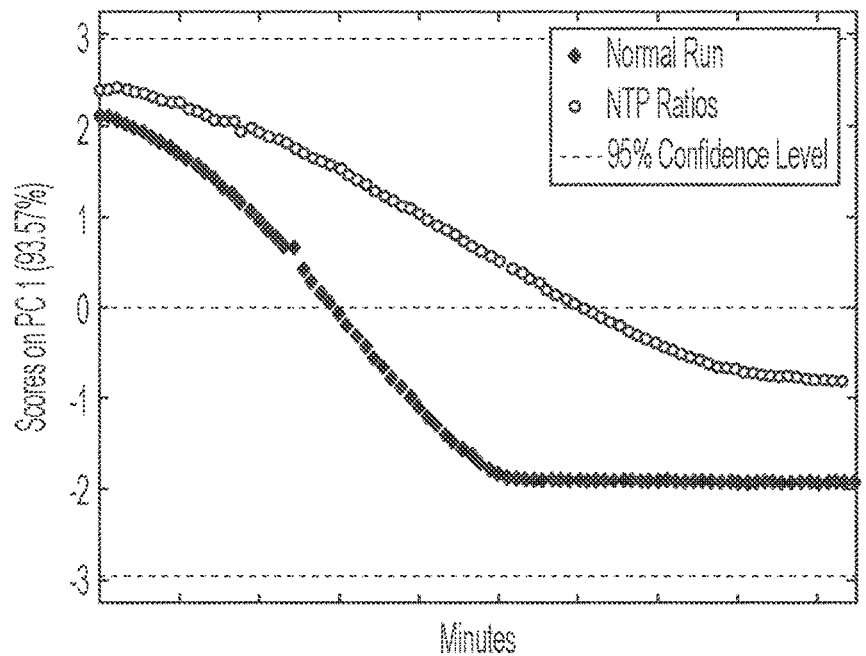
FIG. 5B plots the Scores on PC1 versus time (in minutes) for the two batches from FIG. 5A based on full spectral information using PCA.
Figure 6A:
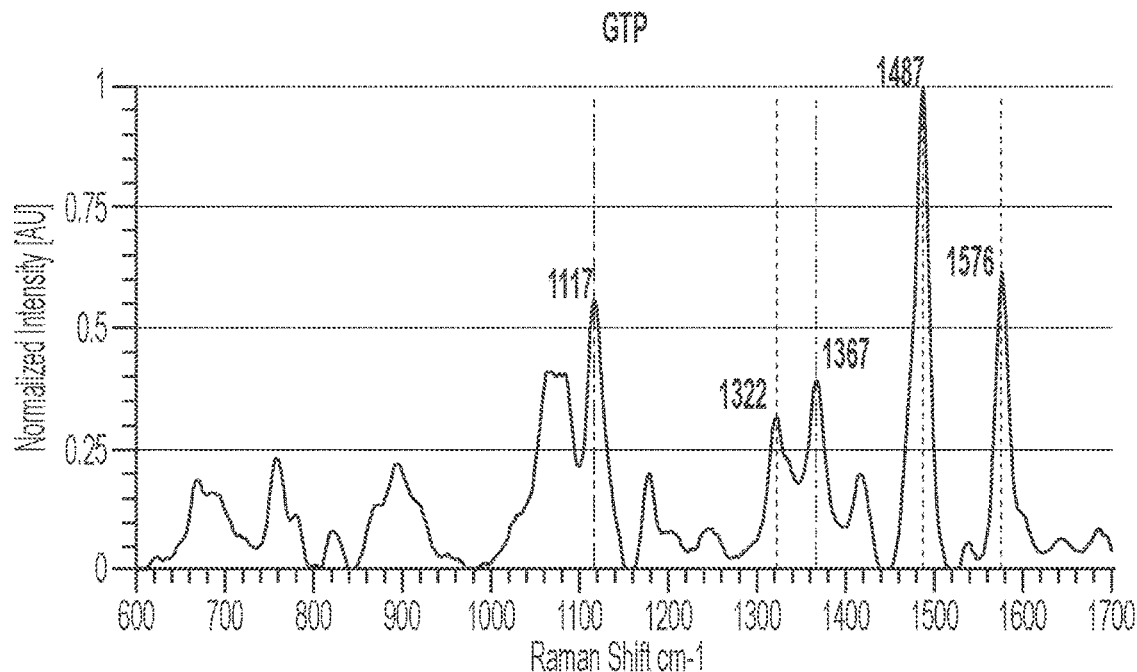
FIG. 6A shows a Raman spectrum for GTP in aqueous solution. Peak identification was limited to intensity greater than 25% of the maximum peak height. Peaks from 1050-1080 $cm^{-1}$ were not included, as these were residual peaks from Tris buffer.
Figure 6B:
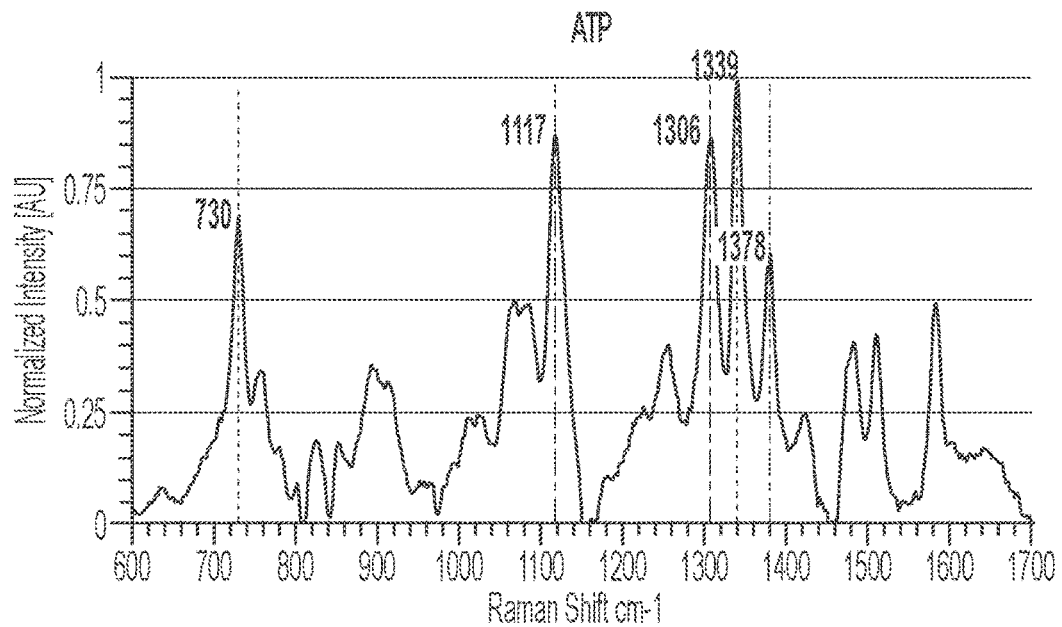
FIG. 6B shows a Raman spectrum for ATP in aqueous solution. Peak identification was limited to intensity greater than 40% of the maximum peak height.
Figure 6C:
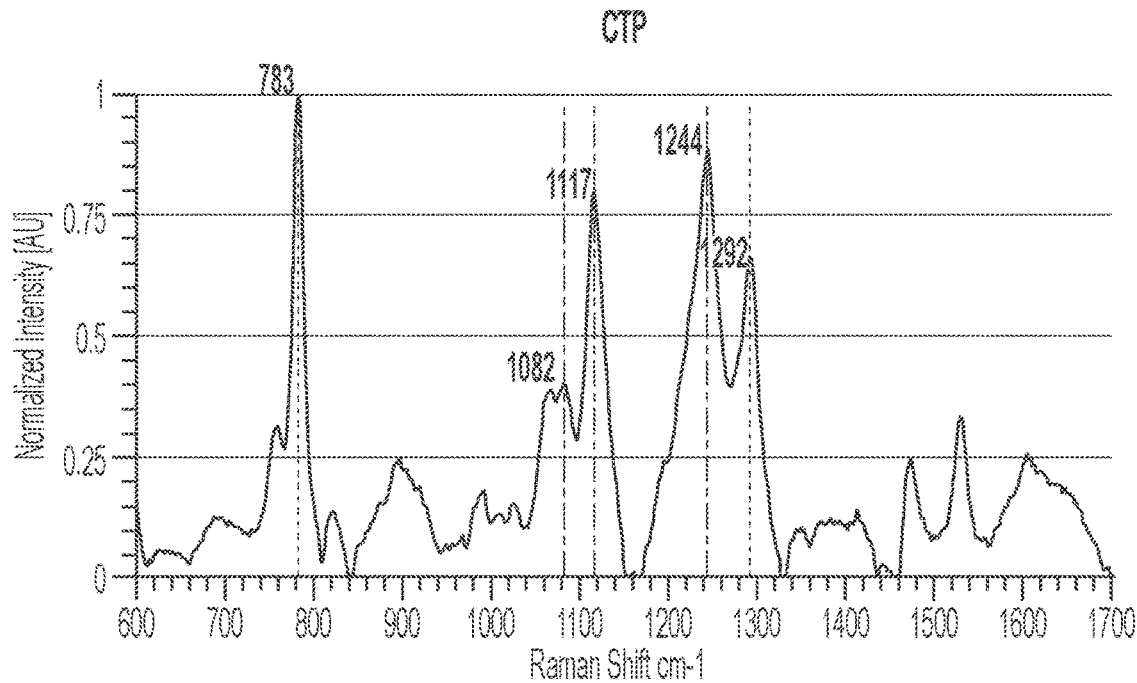
FIG. 6C shows a Raman spectrum for CTP in aqueous solution. Peak identification was limited to intensity greater than 40% of the maximum peak height.
Figure 6D:
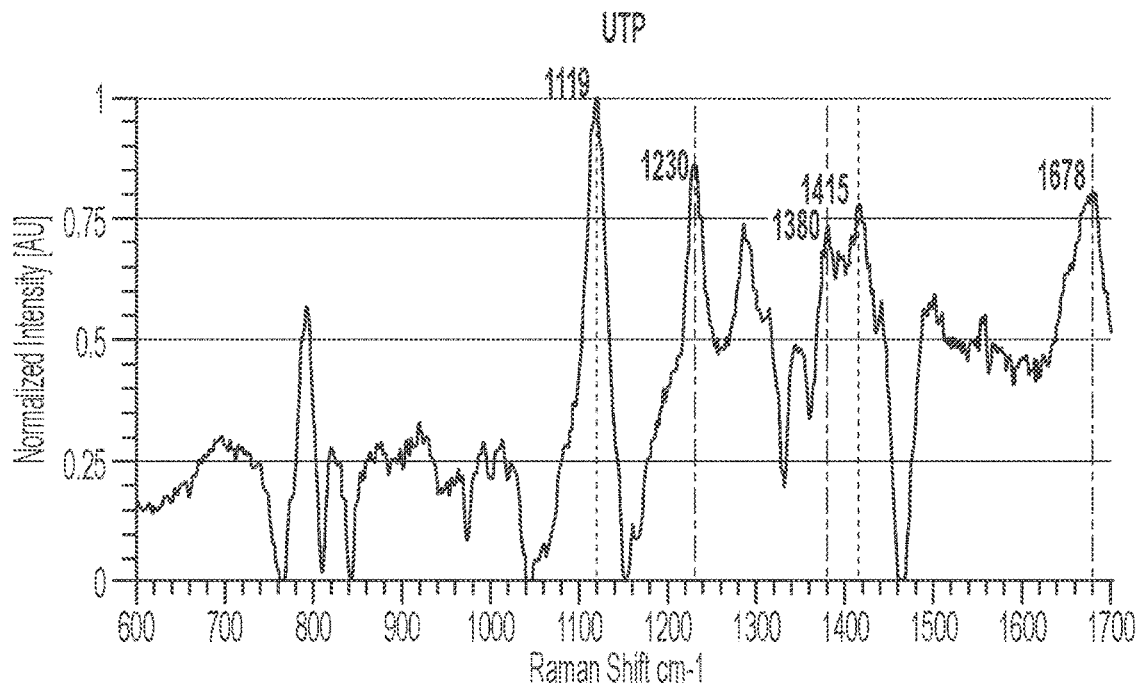
FIG. 6D shows a Raman spectrum for UTP in aqueous solution. Peak identification was limited to intensity greater than 40% of the maximum peak height.

An overlay of all of the spectra obtained for each of the two batches over time is presented in FIG. 5A. As shown in FIG. 5A, certain peaks in the Raman spectrum (e.g., the peaks in the circles in FIG. 5A) of the NTP Ratios batch had different intensities than the same peaks in the normal batch. Moreover, as shown in FIG. 5B, when the Scores on PC1 were plotted versus time (in minutes) for the two batches, there was a substantial difference in the rate of reaction and time of the endpoint for the two batches, with the NTP Ratios batch having a slower rate of reaction and reaching the endpoint much later.

As shown in FIGS. 6A-6D, each individual NTP has a unique Raman spectrum, demonstrating that the presence and/or concentration of individual NTPs may be monitored (e.g., over time) and/or confirmed, in some embodiments.

This example demonstrates that the ratios between the concentrations of NTPs affects the rate of reaction and endpoint time, and that Raman spectroscopy may be used to determine whether the ratios between the concentrations of NTPs are at the desired concentrations (or above or below), in some embodiments.

Example 6

This example describes the monitoring of the presence of desired components (e.g., buffer, NTPs, and/or enzyme solutions) in in vitro transcription of mRNA by monitoring the wavenumber of the largest peak in Raman spectroscopy before in vitro transcription began.

Figure 7:
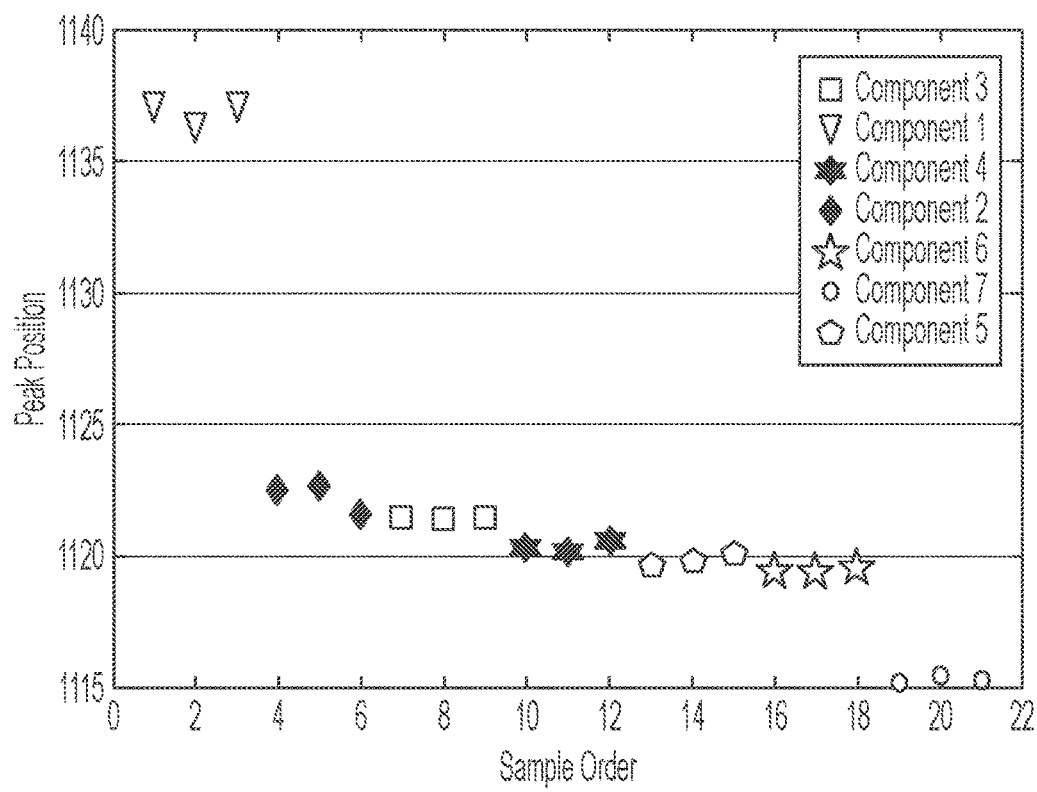
FIG. 7 shows the wavenumber of the largest peak in each Raman spectrum as additional components were individually added for in vitro transcription of mRNA. Spectra were obtained in triplicate after each component was added.

Before in vitro mRNA transcription began, individual components for in vitro transcription were added cumulatively and Raman spectra were obtained. The wavenumber of the largest peak was plotted versus the order of component addition in FIG. 7. Raman spectra were obtained in triplicate after addition of each component. Raman spectra were obtained for a first component of in vitro transcription and the largest peak was found to be around $1137\ cm^{-1}$. A second component was added to the first component and Raman spectra were obtained with a largest peak around $1123\ cm^{-1}$. A third component was then added and Raman spectra were obtained with a largest peak around $1122\ cm^{-1}$. A fourth component was then added and Raman spectra were obtained with a largest peak around $1121\ cm^{-1}$. A fifth component was then added and Raman spectra were obtained with a largest peak around $1120\ cm^{-1}$. A sixth component was then added and Raman spectra were obtained with a largest peak around $1119\ cm^{-1}$. A seventh component was then added and Raman spectra were obtained with a largest peak around $1115\ cm^{-1}$.

This example demonstrates that the presence of one or more (e.g., all) desired components of in vitro transcription may be monitored using Raman spectroscopy by monitoring the wavenumber of the largest peak, in some embodiments.

Example 7

This example describes the monitoring of Tangential Flow Filtration (TFF) by Raman spectroscopy post-in vitro mRNA transcription.

Figure 8:
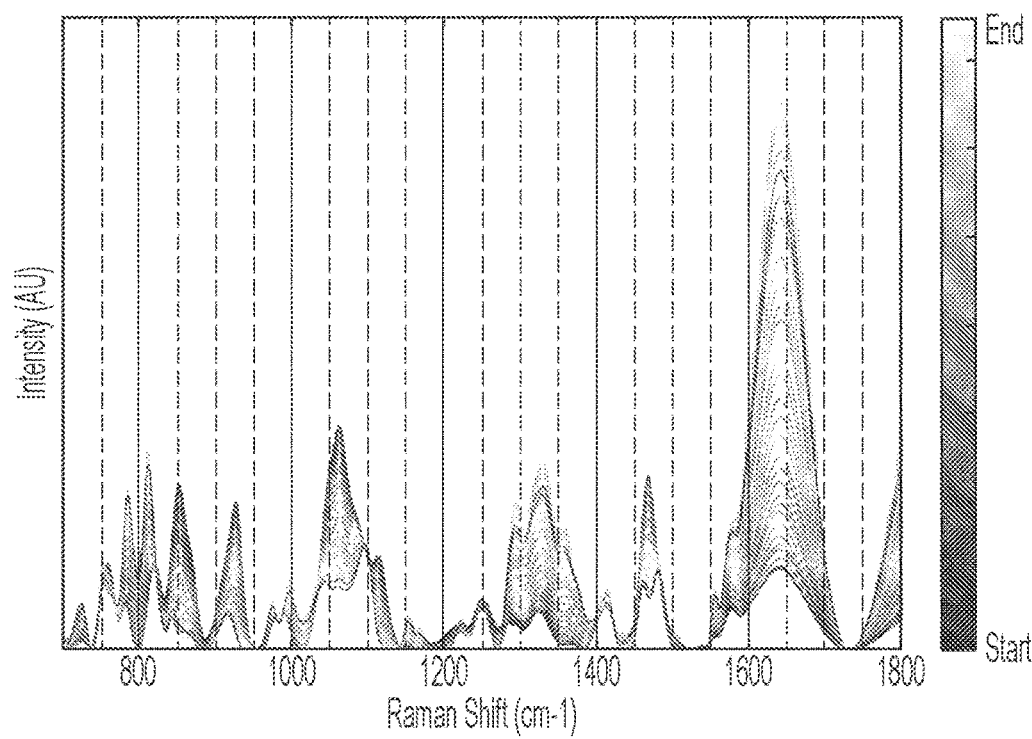
FIG. 8 shows an overlay of Raman spectra (plotting normalized intensity (AU) versus Raman shift ($cm^{-1}$)) during tangential flow filtration of a batch of mRNA post-in vitro mRNA transcription.

After in vitro mRNA transcription was complete. TFF was used to remove residual components of in vitro transcription (e.g., excess starting materials, such as NTPs; enzymes; and/or buffers). Multiple Raman spectra were obtained during the TFF process. As shown in FIG. 8, the Raman spectra changed as TFF progressed. For example, the intensity of peaks associated with residual components of in vitro transcription decreased while the intensity of peaks associated with water and RNA (e.g., the peak around $813\ cm^{-1}$ and the peak around $1100\ cm^{-1}$) increased.

This example demonstrates that post-in vitro mRNA transcription processes such as TFF may be monitored using Raman spectroscopy, in certain embodiments.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed.

Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. "Or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. Each possibility represents a separate embodiment of the present invention.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

To the extent that features are disclosed herein, it will be understood that embodiments comprising, consisting essentially of, and consisting of those features are all encompassed by the present disclosure.

What is claimed is:

1. A method comprising the steps of:
    a) performing in vitro transcription of mRNA;
    b) acquiring one or more Raman spectra during in vitro transcription of mRNA;
    c) determining whether the in vitro transcription has reached a desired endpoint, whether the in vitro transcription is progressing at a desired rate, and/or whether one or more reaction conditions are as desired; and
    d) modifying one or more reaction conditions after the determining step.

2. The method of claim 1, wherein the method further comprises monitoring one or more reaction conditions and/or progression of the in vitro transcription.

3. The method of claim 1, wherein the modifying one or more reaction conditions increases rate of reaction, increases yield, and/or reduces mRNA degradation.

4. The method of claim 1, further comprising (e) stopping the in vitro transcription after the determining step.

5. The method of claim 1, wherein the method comprises using greater than or equal to 1 probe for Raman spectroscopy and less than or equal to 10 probes for Raman spectroscopy.

6. The method of claim 1, wherein the in vitro mRNA transcription comprises a batch process, a fed-batch process, and/or a continuous process.

7. The method of claim 1, wherein the method further comprises monitoring whether all desired components of the in vitro transcription are present.

8. The method of claim 1, wherein the method further comprises performing and/or monitoring one or more post-in vitro transcription processes.

9. The method of claim 8, wherein the method comprises performing and monitoring one or more post-in vitro transcription processes, wherein the monitoring one or more post-in vitro transcription processes comprises monitoring the presence and/or concentration of one or more components of in vitro transcription during the post-in vitro transcription process.

10. A method comprising the steps of:
a) performing in vitro transcription of mRNA;
b) acquiring one or more Raman spectra during the in vitro transcription of mRNA;
c) monitoring one or more reaction conditions and/or progression of the in vitro transcription; and
d) optimizing one of more reaction conditions of a subsequent batch of in vitro transcription based on data generated from the monitoring step.

11. The method of claim 10, wherein the method further comprises determining whether the in vitro transcription has reached a desired endpoint, whether the in vitro transcription is progressing at a desired rate, and/or whether one or more reaction conditions are as desired.

12. The method of claim 10, wherein the one or more reaction conditions comprises temperature, concentration of one or more reactants, concentration of one or more components of one or more enzyme solutions, concentration of one or more components of one or more buffer solutions, and/or rate of mixing.

13. The method of claim 10, wherein the monitoring comprises monitoring formation of one or more byproducts.

14. The method of claim 10, wherein the monitoring comprises monitoring formation of orthophosphate.

15. The method of claim 10, wherein the monitoring comprises monitoring reduction in concentration of one or more reactants.

16. The method of claim 10, wherein the monitoring comprises monitoring reduction in concentration of one or more nucleoside triphosphates (NTPs).

17. The method of claim 10, wherein the monitoring comprises monitoring one or more full Raman spectra.

18. The method of claim 10, wherein the monitoring comprises monitoring one or more peaks of one or more Raman spectra.

19. The method of claim 10, wherein the monitoring comprises monitoring one or more peaks at greater than or equal to 970 $cm^{-1}$ and less than or equal to 1000 cm 1 of one or more Raman spectra.

20. The method of claim 10, wherein the monitoring comprises monitoring one or more peaks at greater than or equal to 1100 $cm^{-1}$ and less than or equal to 1120 $cm^{-1}$ of one or more Raman spectra.

21. The method of claim 10, wherein the monitoring comprises monitoring one or more peaks at greater than or equal to 1150 $cm^{-1}$ and less than or equal to 1650 $cm^{-1}$ of one or more Raman spectra.

22. The method of claim 10, wherein the monitoring comprises monitoring one or more peaks at greater than or equal to 800 $cm^{-1}$ and less than or equal to 880 $cm^{-1}$ of one or more Raman spectra.

23. The method of claim 10, wherein the monitoring comprises monitoring one or more peaks at greater than or equal to 920 $cm^{-1}$ and less than or equal to 940 $cm^{-1}$ of one or more Raman spectra.

24. The method of claim 10, wherein the monitoring comprises monitoring one or more peaks at greater than or equal to 1040 $cm^{-1}$ and less than or equal to 1070 $cm^{-1}$ of one or more Raman spectra.

25. The method of claim 10, wherein the monitoring comprises using an algorithm to determine whether the in vitro transcription has reached a desired endpoint, whether the in vitro transcription is progressing at a desired rate, and/or whether one or more reaction conditions are as desired.

26. The method of claim 25, wherein the algorithm comprises Principal Component Analysis (PCA) and/or a Batch Evolution Model.

27. The method of claim 10, wherein the monitoring comprises comparing one or more Raman spectra and/or representations thereof to one or more reference Raman spectra and/or representations thereof to identify the presence of one or more differences.

28. The method of claim 27, wherein the method further comprises identifying the cause of the one or more differences that are present.

29. The method of claim 10, wherein the monitoring comprises monitoring a peak representative of mRNA.

30. The method of claim 10, wherein the method comprises using greater than or equal to 1 probe for Raman spectroscopy and less than or equal to 10 probes for Raman spectroscopy.

* * * * *